United States Patent [19]

Kammerer et al.

[11] Patent Number: 5,681,324
[45] Date of Patent: Oct. 28, 1997

[54] SURGICAL TISSUE RETRIEVAL INSTRUMENT

[75] Inventors: Gene W. Kammerer, East Brunswick; Royce Frederick, So. Bound Brook; Barbara Howard, Plainfield; Edd Walker, Stockton, all of N.J.

[73] Assignee: Ethicon, Inc., Somerville, N.J.

[21] Appl. No.: 484,225

[22] Filed: Jun. 7, 1995

Related U.S. Application Data

[62] Division of Ser. No. 78,881, Jun. 16, 1993, Pat. No. 5,480,404.

[51] Int. Cl.⁶ ..................... A61B 17/00
[52] U.S. Cl. ..................... 606/113; 606/114
[58] Field of Search ........... 128/749; 600/37; 606/113, 114, 127

[56] References Cited

U.S. PATENT DOCUMENTS

| | | | |
|---|---|---|---|
| 1,606,497 | 11/1926 | Berger | 606/113 |
| 3,181,533 | 5/1965 | Heath | 606/113 |
| 5,163,942 | 11/1992 | Rydell | 606/113 |
| 5,190,555 | 3/1993 | Wetter et al. | 606/113 |
| 5,201,740 | 4/1993 | Nakao et al. | 606/113 |
| 5,312,416 | 5/1994 | Spaeth et al. | 606/113 |

*Primary Examiner*—Max Hindenburg
*Attorney, Agent, or Firm*—Emil Richard Skula

[57] ABSTRACT

A surgical tissue retrieval instrument has a collapsible pouch at the distal end of an elongated support tube for retrieving internal body tissue through a trocar tube. The instrument includes a belt which is formed into a loop slidably attached about the open end of the pouch. The belt is slidably extendable through the support tube for expanding the open end of the pouch to receive the tissue and retractable into the support tube for drawing the open end of the pouch closed to enclose the tissue in the pouch. The belt has an oblong, e.g., rectangular, cross section oriented with its larger cross-sectional dimension perpendicular to the plane of the loop to provide stability at the open end of the pouch and to enable use of the pouch in a scoop-like manner to place the tissue therein. A portion of the belt is thermally set into a curved configuration to urge the loop into a normally expanded shape with the belt extended from the distal end of the support tube. A belt actuator mechanism includes a reciprocating finger grip and a ratchet mechanism which operates in a toggle-like manner to advance and retract the belt along the support tube to open and close the pouch. The pouch has an elongated tapered shape to align the tissue with the length or depth of the pouch to facilitate the withdrawal of the pouch and tissue through an incision at the trocar site.

6 Claims, 18 Drawing Sheets

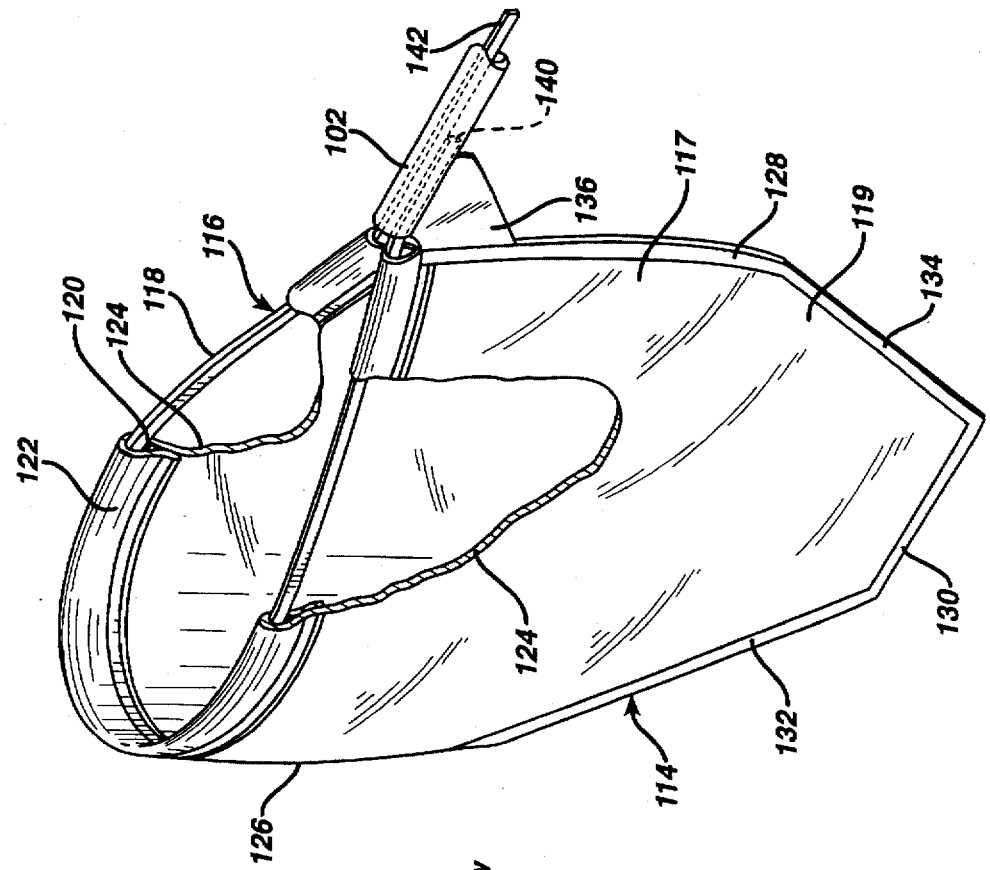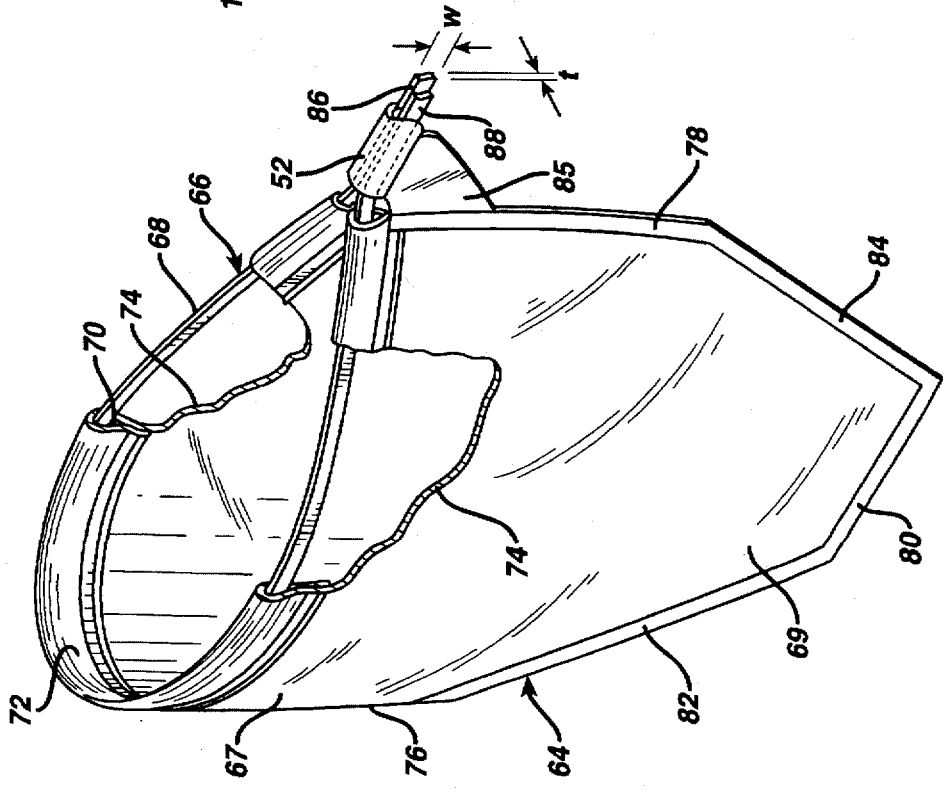

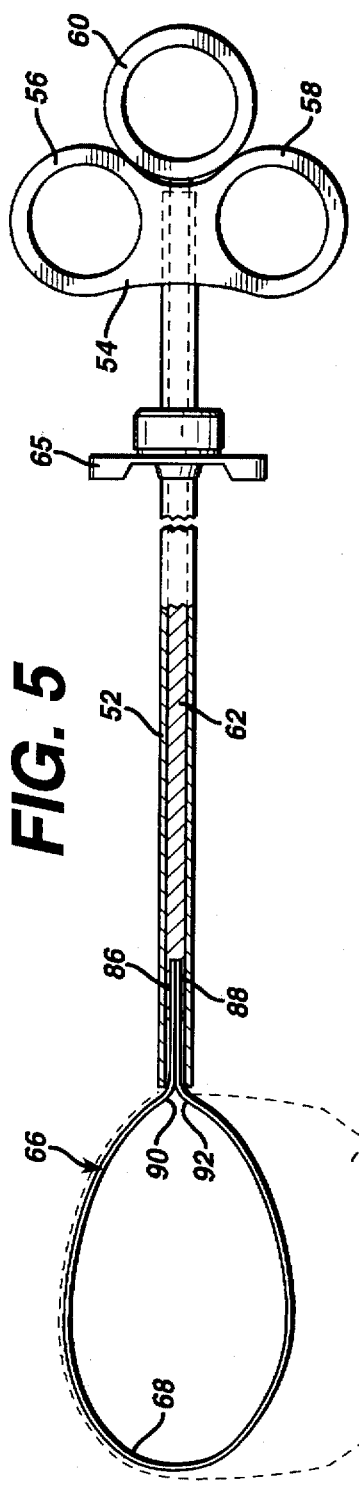
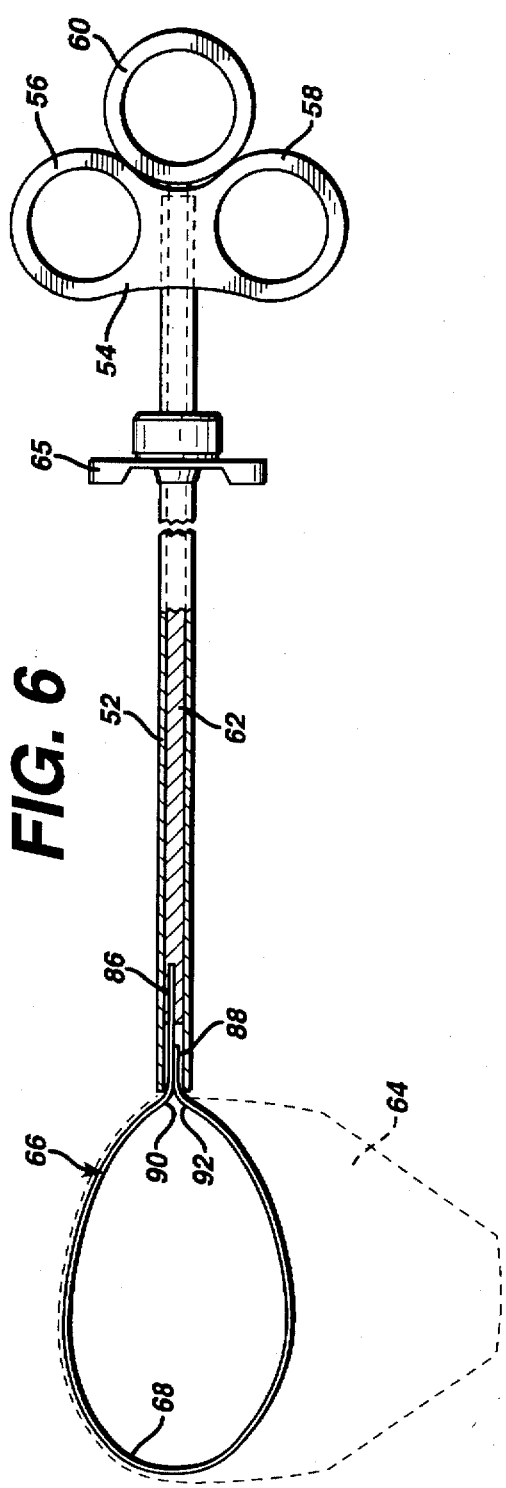

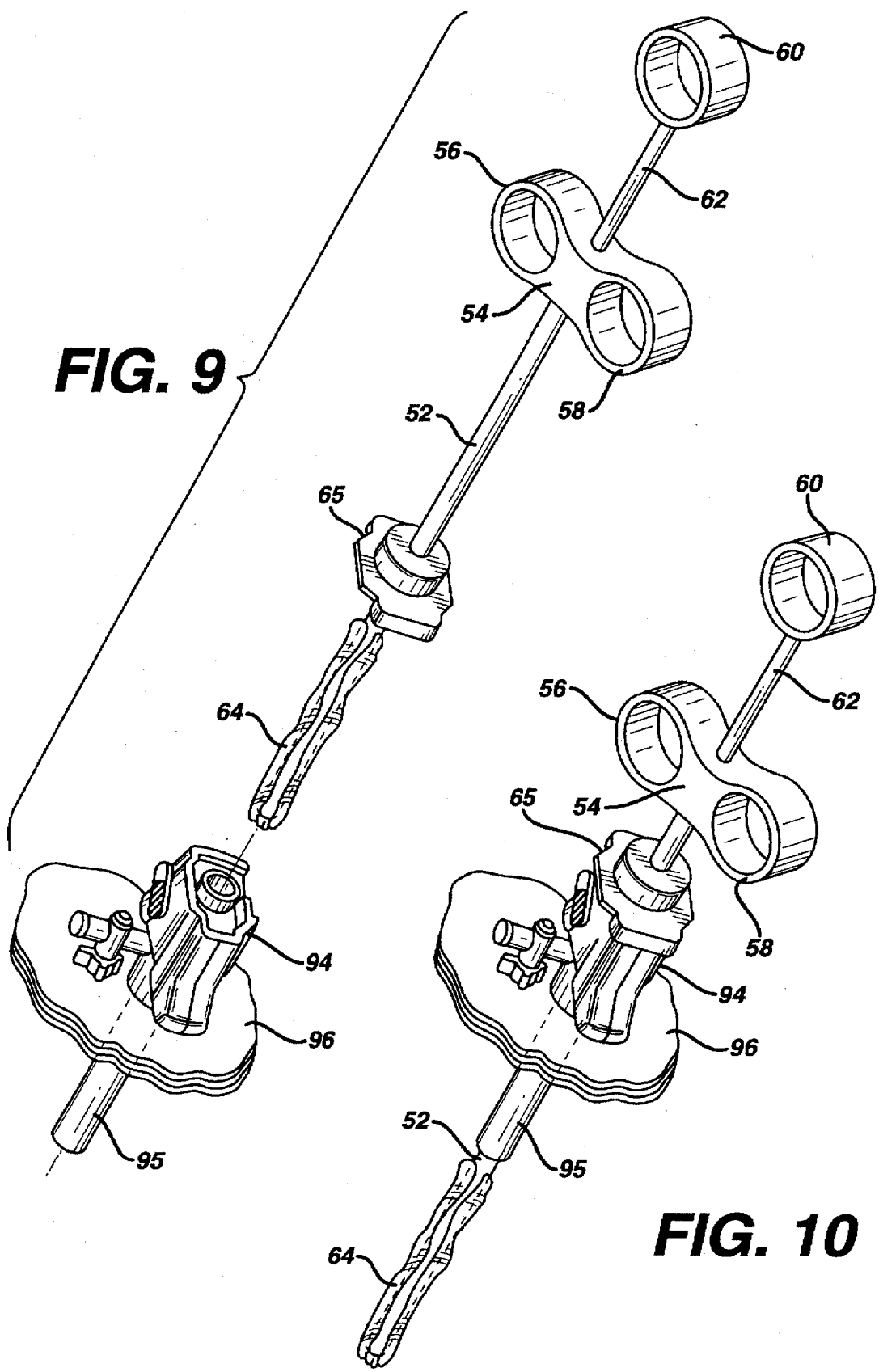

5,681,324

SURGICAL TISSUE RETRIEVAL INSTRUMENT

This is a division of application Ser. No. 08/078,881, filed Jun. 16, 1993 U.S. Pat. No. 5,480,404, which is hereby incorporated by reference.

FIELD OF THE INVENTION

The present invention relates to a surgical instrument for retrieving internal body tissue and, more particularly, to a surgical instrument used in endoscopic surgery for retrieving internal body tissue through a trocar or endoscopic tube.

BACKGROUND OF THE INVENTION AND PRIOR ART

Surgical pouches have been developed for use in laparoscopic surgery to remove tissue specimens from the abdominal cavity. The purpose of the pouch is to keep the tissue specimen intact as it is removed through the trocar site in the abdominal wall. Typically, these pouches have been made from a polymeric film. Usually, these devices employ a closure means at the open end or mouth of the pouch to prevent spillage of tissue or fluids into the abdomen. For example, the closure means has been described in the prior art as a thread or suture which passes around the mouth of the pouch through a channel formed by a folded edge which is heat sealed to the side of the pouch. Also, the closure means has been described as a wire arranged in a single or double loop.

Although the surgical pouches of the prior art have been developed for the removal of the tissue from the abdomen through an incision at a trocar site, there has been a problem in the placement of the tissue into the pouch prior to the closure and removal of the pouch from the abdominal cavity. In the prior art devices, the mouth of the pouch does not remain wide open and the lack of stability at the mouth makes it difficult to accomplish the desired positioning of the pouch inside the body cavity. Because of these factors, it is necessary for the surgeon to use a first grasper to hold the mouth of the pouch and a second grasper to attempt to place the tissue into the pouch. The need for the additional grasper may require the insertion of an extra trocar tube into the abdominal wall.

Another problem associated with the devices of the prior art is inability of the closed pouch to be opened or reopened inside the body cavity. In the prior art devices which employ a thread or wire as the closure or cinching mechanism, once the pouch is closed about the tissue specimen, the pouch cannot be opened until the pouch is removed from the body cavity. This problem arises because of the difficulty in loosening the knot at the base of the wire loop and in removing the wire from the channel around the mouth of the pouch.

Examples of surgical retrieval devices with drawstrings for closing the pouches are disclosed in U.S. Pat. Nos. 5,037,379 and 5,143,082. Clayman et al U.S. Pat. No. 5,037,379 discloses a surgical tissue bag including a drawstring for drawing the open end of the bag closed and for pulling the closed open end of the bag from a body cavity through a trocar sheath. Kindberg et al U.S. Pat. No. 5,143,082 discloses a surgical device for enclosing an internal body organ or tissue which includes a filamentary strand extending through a tubular sleeve and formed into a noose abut the open end of a surgical bag. The noose is secured by a knot which allows the strand to be pulled into the tubular sleeve to close the surgical bag and which prevents the noose from loosening when engaged about an internal body organ or tissue. Neither of these examples discloses any mechanism to enhance the stability of the drawstrings.

Wetter et al U.S. Pat. No. 5,190,555 discloses another example of an endoscopic tissue retrieval device for the collection and removal of internal body parts including a drawstring used for closing and opening a flexible funnel-shaped sack. The device includes a tubular member of relatively rigid material provided with a longitudinal slot in which a side portion of the flexible sack is secured. No mention is made of any arrangement to enhance the stability of the drawstring.

Rydell U.S. Pat. No. 5,163,942 discloses a surgical grasping instrument including a belt which forms an extendable and retractable grasping loop for laparoscopic procedures. The instrument is used to rotate an internal organ or tissue about the longitudinal axis of the instrument or about an axis transverse to the longitudinal axis. The Rydell instrument is used to grasp and manipulate internal organs, e.g., the gallbladder, during cauterization, but no pouch is provided to enclose and retrieve the tissue.

Nakao et al U.S. Pat. No. 5,190,542 discloses a surgical instrument for use in snare cauterization including a flexible web member which forms a capture pocket and a flexible cauterization loop at the mouth of the pocket. The cauterization loop is extendable and retractable into a sheath member to open and close the flexible web member. The sheath member is retractable through an endoscope to remove the cauterized tissue. A flexible auxiliary loop of synthetic resin or polymeric material is disclosed, but no provision is made to stabilize the cauterization loop.

An object of the present invention is to provide an improved tissue retrieval instrument for use in endoscopic surgery.

Another object of the invention is to provide a surgical instrument for retrieving internal body tissue having a collapsible pouch and a cinching mechanism which enhances the stability of the open end of the pouch when expanded inside a body cavity to facilitate the tissue placement in the pouch.

A further object of the invention is to provide a tissue retrieval instrument including a collapsible pouch and a cinching mechanism which enables the pouch to be reopened inside the body cavity to receive additional pieces of tissue.

It is another object of the invention to provide an endoscopic instrument for retrieving internal body tissue including a collapsible pouch and a cinching mechanism in the form of a belt with an oblong or rectangular cross section to enhance the stability of the open end of the pouch in its expanded configuration.

Another object of the invention is to provide a surgical instrument for retrieving internal body tissue including a collapsible pouch, a belt formed into a loop attached about the open end of the pouch, and a ratchet mechanism for advancing and retracting the belt to expand and contract the open end of the pouch.

It is a further object of the invention to provide an endoscopic instrument for retrieving internal body tissue including a collapsible pouch which is tapered and elongated to align the tissue in a desired orientation in the pouch to facilitate the passage of the tissue through a trocar site.

SUMMARY OF THE INVENTION

The present invention provides an improved surgical tissue retrieval instrument for use in endoscopic surgery which overcomes the drawbacks of the prior art by using a belt as the draw down or cinching mechanism for the open end of the pouch. The advantage of a belt cinching mechanism is that the belt has an oblong, e.g., rectangular, cross section which can be made thin and flexible in one direction (thickness) and wide and rigid in the other direction (width). Also, the bolt has a high columnar strength which enables it to be used to exert pressure at one end by applying a force at the other distant end. In contrast to wires or threads, a belt has structural properties associated with its cross section which can be modified to change its bending, recovery and rigidity characteristics to provide a pouch cinching mechanism with sufficient stability to retain the mouth of the pouch open inside the body cavity and to enable the pouch to be used in a scoop-like manner to facilitate the placement of the tissue into the pouch.

In accordance with the present invention, a surgical instrument for retrieving tissue comprises an elongated support shaft, a collapsible pouch supported at the distal end of the support shaft and having an open end for receiving the tissue to be retrieved, and a belt attached abut the open end of the pouch and slidable longitudinally relative to the support shaft for expanding the open end of the pouch to receive the tissue and for drawing the open end of the pouch closed to enclose the tissue in the pouch. The belt has an oblong cross section oriented to enhance the stability of the open end of the pouch. The belt is formed into a loop extending from the distal end of the support shaft about the end of the pouch. The oblong cross section of the belt is oriented with its larger cross-sectional dimension perpendicular to the plane of the loop. Preferably, a portion of the belt is preformed to urge the loop into a normally expanded shape to hold the pouch open to receive the tissue therein. For example, the preformed portion of the belt is thermally set into a curved configuration to urge the loop into a normally expanded shape with the belt extended from the distal end of the support shaft.

In a preferred embodiment of the surgical instrument for retrieving internal body tissue, a collapsible pouch is supported at the distal end of a support tube and has an open end for receiving the tissue to be retrieved. A belt is formed into a loop slidably attached abut the open end of the pouch. The belt is slidably extendable through the support tube for expanding the open end of the pouch to receive the tissue and retractable into the support tube for drawing the open end closed to enclose the tissue in the pouch. The belt has an oblong cross section oriented to provide stability at the open end of the pouch to enable use of the pouch in a scoop-like manner to place the tissue therein. The oblong cross section of the belt is oriented with its larger cross-sectional dimension perpendicular to the plane of the loop to resist bending in a direction perpendicular to the plane of the loop.

In one example of a pouch cinching mechanism, both ends of the belt are slidably received in the support tube and attached to an actuator slidably mounted therein for simultaneously moving the belt ends along the support tube to expand and contract the loop. Alternatively, one end of the belt is attached to the belt itself to define the loop and the other end of the belt is attached to an actuator slidably mounted in the support tube for moving the other end of the belt along the support tube to expand and contract the loop. In another embodiment, one end of the belt is attached to the support tube and the other end of is attached to an actuator slidably mounted in the support tube for moving the other end of the belt along the support tube to expand and contract the loop.

Preferably, the belt has one or more preformed curvatures which urge the loop into an expanded shape when the belt is extended from the distal end of the support tube. Alternatively, guide means is provided at the distal end of the support tube for engaging the belt and urging the loop into an expanded shape when the belt is extended from the distal end of the support tube.

Another aspect of the invention relates to an improved surgical tissue retrieval instrument which employs a reciprocating ratchet means for actuating the pouch cinching mechanism to selectively expand and contract the open end of the pouch. The ratchet means is embodied as a reciprocating finger grip slidably mounted for longitudinal movement relative to the support tube and a ratchet mechanism on the finger grip for selectively advancing and retracting the belt to expand and contract the loop at the open end of the pouch. Preferably, the ratchet mechanism comprises a trigger pivotally mounted on the finger grip and including first teeth for engaging and advancing the belt and second teeth for engaging and retracting the belt relative to the support tube, and a switch for controlling the pivoting of the trigger to determine which teeth engage the belt when the finger grip is reciprocated.

In a preferred embodiment of the ratchet mechanism, a finger actuated trigger is pivotally mounted on the finger grip and includes first teeth for engaging and advancing the belt when the trigger is pivoted to a first position and second teeth for engaging and retracting the belt when the trigger is pivoted to a second position. The trigger is normally located in a neutral position with both of the teeth disengaged from the belt. A switch is mounted on the finger grip for control of the pivoting of the trigger to determine which of the teeth engage the belt when the finger grip is reciprocated. The switch has a neutral position in which the trigger is maintained in its neutral position, a first operative position in which the trigger is pivotable in a toggle-like manner between its neutral position and its first position when the finger grip is reciprocated to advance the belt and expand the loop, and a second operative position in which the trigger is pivotable in a toggle-like manner between its neutral position and its second position when the finger grip is reciprocated to retract the belt and contract the loop.

A further aspect of the invention relates to an improved surgical tissue retrieval instrument including a collapsible pouch with a tapered shape for aligning the tissue in a desired orientation in the pouch to facilitate the passage of the tissue through an incision at a trocar site. Preferably, the collapsible pouch is elongated in shape with a length or depth substantially greater than its width at the open end of the pouch. A preferred embodiment of the pouch has an upper straight portion with parallel sides adjacent to its open end and a lower tapered portion with converging sides. The upper straight portion facilitates the complete expansion of the open end of the pouch for placement of the tissue therein. The lower tapered portion causes the tissue to align itself with the length or depth of the pouch and facilitates the removal of the pouch and tissue from the body cavity through the trocar site.

BRIEF DESCRIPTION OF THE DRAWINGS

The foregoing and other objects, aspects and advantages will be better understood from the following detailed description of the preferred embodiments of the invention with reference to the drawings, in which:

FIG. 3 is an enlarged, partially cutaway perspective view showing a tissue receiving pouch of the surgical instrument of FIG. 1;

FIG. 4 is an enlarged, partially cutaway perspective view showing a tissue receiving pouch of the surgical instrument of FIG. 2;

FIG. 5 is a partially cutaway plan view of the surgical instrument of FIG. 1;

FIG. 6 is a partially cutaway plan view of a modification of the instrument of FIG. 5;

FIGS. 9–14 illustrate the operation of the surgical instrument of FIG. 1 to retrieve a piece of internal body tissue through a trocar site.

DETAILED DESCRIPTION OF PREFERRED EMBODIMENTS

Figure 1:
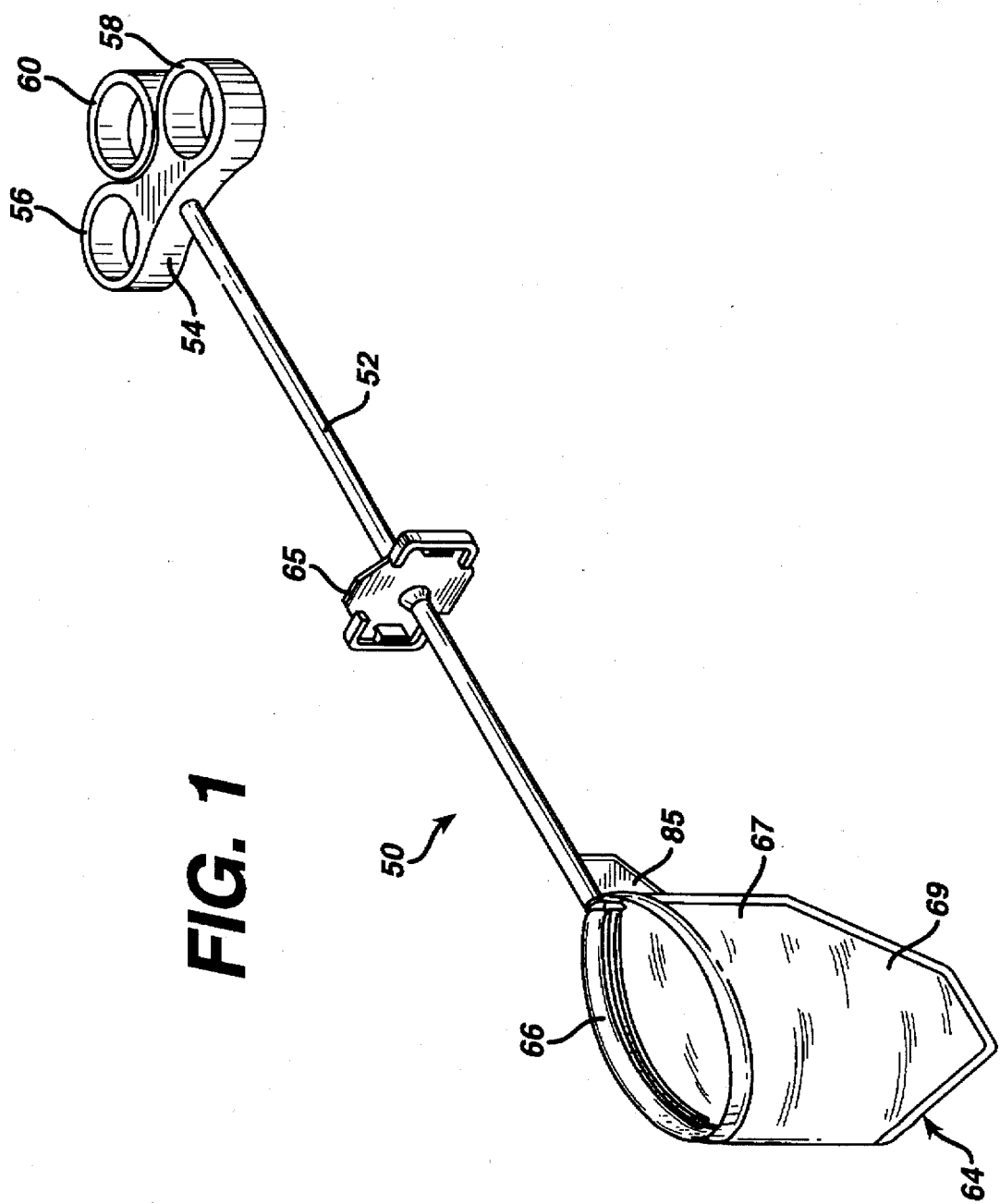
FIG. 1 is a perspective view of a first embodiment of a surgical instrument for retrieving internal body tissue constructed in accordance with this invention.

Referring to FIG. 1, the present invention is embodied in a surgical instrument, generally 50, for retrieving internal body tissue through a trocar or endoscopic tube inserted into the body wall of a patient. The surgical instrument 50 includes an elongated support tube 52 mounted on a finger grip 54 at the proximal end of the support tube 52. The finger grip 54 includes a pair of finger receiving rings 56 and 58. A thumb ring 60 is mounted at the proximal end of an acutator rod 62 (FIG. 5) which is slidably received within the support tube 52. At the distal end of the support tube 52, a collapsible pouch 64 is supported by a flexible belt 66 which is slidably received in the support tube 52 and secured to the actuator rod 62.

The pouch 64 has an open top end or mouth for receiving a piece of tissue to be retrieved. The belt 66 is attached about the open end of the pouch 64 and is slidably extendable through the support tube 52 for expanding the open end of the pouch 64 to receive the tissue and for drawing the open end closed to enclose the tissue in the pouch 64. The distal end of the support tube 52 is sufficiently small in diameter to effectively prevent the pouch material from entering the tube 52 when the mouth of the pouch 64 is cinched by retracting the belt 66 into the tube 52. The support tube 52 is sized for insertion through a trocar or endoscopic tube into a body cavity. An adapter 65 is slidably mounted on the support tube 52. The adapter 65 is arranged to provide a snap fit with the trocar tube and to provide a sliding seal with the support tube 52 to maintain the pressure within the body cavity. With the pouch 64 closed, the surgical instrument 50 is inserted through the trocar or endoscopic tube into the body cavity. After the insertion of the surgical instrument 50 into the body cavity, the pouch 64 is opened and a piece of internal body tissue is placed therein. After the pouch 64 is closed, the surgical instrument 50 is withdrawn from the body cavity with the trocar or endoscopic tube to remove the tissue from the body.

Referring to FIG. 3, the bolt 66 is flexed to form a loop 68 extending from the distal end of the support tube 62. The loop 68 is slidably received within a channel 70 which extends along the circumferential length of the open end of the pouch 64. The channel 70 is formed by folding the top portion of the pouch 64 inwardly over itself to provide a circumferential flap 72 which is sealed along its lower edge to the opposed side walls 74 of the pouch 64. The side walls 74 are folded toward each other about a distal edge 76 of the pouch 64. The side walls 74 of the pouch 64 are hermetically sealed together along a proximal edge 78, a bottom edge 80, and a pair of tapered edges 82 and 84. Preferably, the bottom of the pouch 64 is tapered along the edges 82 and 84 to provide a shape which tends to align a piece of tissue placed in the pouch 64 in a convenient orientation for removal through the incision at the trocar site when the pouch 64 is closed and the instrument 50 is withdrawn. The pouch 64 has a proximal flap 85 adjacent to its open top end which is secured to the distal end of the support tube 52, e.g., by glue, epoxy, hot melt or another conventional adhesive bonding arrangement. Alternatively, the pouch 64 can be secured at its proximal edge by a suture (not shown), which can be threaded through the pouch material and attached at the distal end of the support tube 52, or by a clip.

The belt 66 comprises an elongated flexible member of plastic material which is slidably received in the support tube 52. The belt 66 has an oblong cross section oriented to enhance the stability of the open end of the pouch 64 when the belt 66 is extended. Preferably, the bolt 66 is substantially rectangular in cross section with a width larger than its thickness. For example, the belt 66 has a width w in the range of 0.050 inch to 0.160 inch and a thickness t in the range of 0.020 inch to 0.60 inch. A preferred embodiment of the belt 66 consists of nylon with a width of 0.100 inch and a thickness of 0.030 inch. The larger dimension, i.e., the width w of the belt 66, is oriented perpendicular to the plane of the loop 68 and parallel to the side walls 74 of the pouch 64. By movement of the thumb ring 60 relative to the finger grip 54, the belt 66 is extendable from the distal end of the support tube 52 to expand the loop 68 to open the pouch 64 and is retractable into the support tube 52 to contract the loop 68 to draw the open end of the pouch 64 closed to enclose the tissue therein.

Preferably, the belt 66 consists of a single continuous flexible plastic member which is formed by extrusion. The material of the belt 66 consists of a flexible polymeric material such as nylon, polypropylene, urethane, polyethylene or other similar plastic material. The belt 66 can also be made from a composite of one or more of these materials with supporting wires, fibers, or yarns included in the belt 66 to assist in any deformation which may occur due to the bending of the belt 66. The supporting wires or fibers are generally embedded into the belt 66 and extend parallel to the longitudinal axis of the belt 66. Preferably, the supporting wires or fibers consist of materials which exhibit a high bending modulus, such as stainless steel, Kevlar or fiberglass.

The pouch 64 is made from a polymeric material which is formed into a film. The film is shaped into the desired configuration for the pouch 64 and is sealed along the edges 78, 80, 82 and 84 by the application of heat or radio frequency energy. Although the pouch 64 can be made in various shapes, it has been found that a tapered shape for the pouch 64 is desirable. Preferably, the pouch 64 has a top straight portion 67 with substantially parallel sides and a bottom tapered portion 69 with converging sides. The top straight portion 67 permits the complete expansion of the mouth of the pouch 64 and the belt loop 68. The bottom tapered portion 69 of the pouch 64 forces the tissue specimen to align itself with the length of the pouch 64 and facilitates the removal of the pouch 64 and tissue specimen from the body cavity through the trocar port site. The tapered shape of the pouch 64 makes it possible to remove tissue from the body cavity without enlarging the incision at the trocar site. The tapered pouch 64 represents an improvement over a square bottom pouch where the tissue specimen can lay across the width of the pouch and impede removal through the trocar site. The tapered pouch shape also reduces the amount of trapped air, thereby reducing the ballooning effect when the pouch 64 is closed and the stress exerted on the pouch 64 and the abdominal wall tissue at the trocar site.

In the embodiment of FIG. 5, both ends 86 and 88 of the belt 66 are slidably received in the support tube 52 and are secured to the distal end of the slidable actuator rod 62. When the actuator rod 62 is pulled in the proximal direction, the loop portion 68 is quickly closed because both ends 86 and 88 of the belt 66 are pulled through the support tube 52 at the same time. Preferably, the portion of the belt 66 extending from the distal end of the support tube 52 is preformed to urge the loop 68 into a normally expanded shape to hold the pouch 64 open to receive the tissue therein. To maintain the roundness of the loop 68 after it is closed and re-opened, the entire loop portion 68 of the belt 66 is thermally set into a generally circular expanded shape. The belt 66 is provided with a pair of opposed thermally set curvatures 90 and 92 at the base of the loop 68 which urge the loop 68 into a generally circular, open position when the belt 66 is extended from the support tube 52. Also, the curvatures 90 and 92 counteract the deformation of the material of the belt 66 which may occur at the apex of the loop 68 when the belt 66 is pulled into the support tube 52 to close the loop 68 to its smallest diameter. Alternatively, the belt 66 can be preformed by injection molding to provide the curvatures 90 and 92 in the loop 68.

Figure 8:
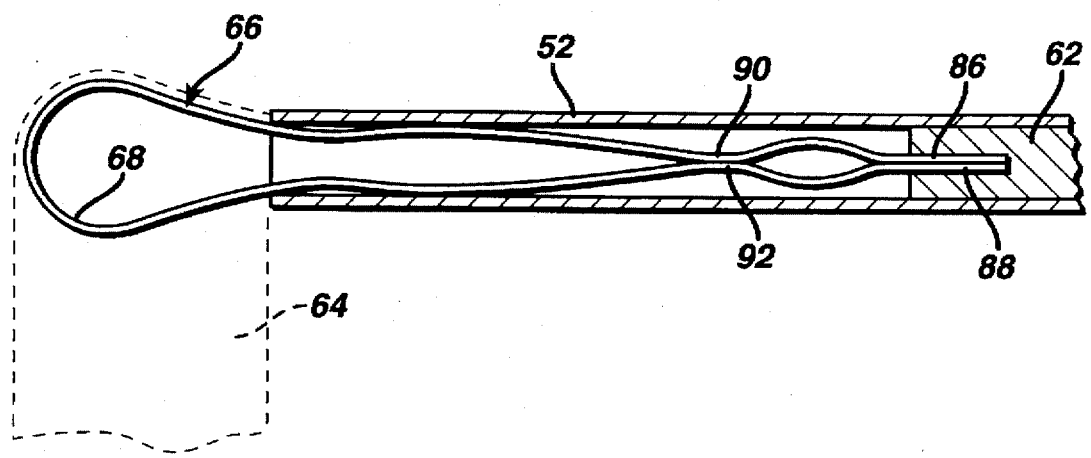
FIG. 8 is an enlarged fragmentary section showing the operation of the surgical instrument of FIG. 5.

Referring to FIG. 8, when the actuator rod 62 is retracted into the support tube 52, the belt ends 86 and 88 are pulled in the proximal direction and the thermally set curvatures 90 and 92 are drawn into the distal end of the support tube 52 to contract the loop 68 and to close the open end of the pouch 64. The thermally set curvatures 90 and 92 are held in contact with each other inside the support tube 52 and generate biasing forces to urge the belt 66 into frictional engagement with the inner wall of the support tube 52. These biasing forces frictionally maintain the actuator rod 62 in its retracted position with the loop 68 contracted into the support tube 52. When the actuator rod 62 is advanced, the thermally set curvatures 90 and 92 emerge from the distal end of the support tube 52 and return the loop 68 to its expanded shape to open the mouth of the pouch 64.

In the modification of FIG. 6, only one end 86 of the belt 66 is secured to the actuator rod 62. The other belt end 88 is secured to one side of the belt 66 itself to form the distal belt loop 68. The belt 66 has preformed portions, e.g., a pair of thermally set curvatures 90 and 92 at the base of the loop 68, which urge the loop 68 into a generally circular, open position when the belt 66 is extended from the support tube 52. Also, the thermally set curvatures 90 and 92 generate biasing forces which urge the belt 66 into frictional engagement with the inner wall of the support tube 52 when the actuator rod 62 is retracted into the support tube 52.

Figure 7:
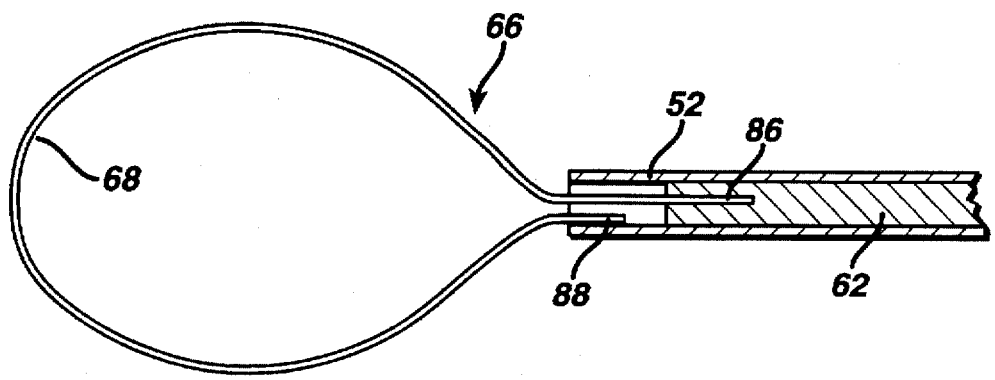
FIG. 7 is a partially cutaway plan view of another modification of the instrument of FIG. 5.

In the embodiment of FIG. 7, one end 88 of the belt 66 is attached adjacent to the distal end of the support tube 52. For example, the distal belt end 88 can be secured inside the distal end of the support tube 52. The belt 66 is flexed to form the loop 68 which extends distally from the support tube 52. The other proximal end 86 of the belt 66 extends longitudinally into the support tube 52 and is secured to the distal end of the actuator rod 62. By pulling on the thumb ring 60 at the proximal end of the actuator rod 62, the belt 66 is pulled in the proximal direction along the support tube 52 to contract the loop 68 and to close the open end of the pouch 64. By pushing on the thumb ring 60, the actuator rod 62 is advanced distally along the support tube 52 to expand the loop 68 to open the mouth of the pouch 64.

Referring to FIGS. 9-14, the instrument 50 is used to retrieve a piece of internal body tissue through a trocar port 94 including a trocar tube 95 inserted into an incision in a body wall 96. Prior to the insertion of the instrument 50 into the trocar tube 95, the mouth of the pouch 64 is closed by pulling the finger ring 60 in the proximal direction to contract the belt loop 68 into the support tube 52 (FIG. 9). With the pouch 64 aligned with the longitudinal axis of the support tube 52, the distal end of the support tube 52 is inserted into the trocar tube 95 and advanced until the entire pouch 64 exits from the trocar tube 95 into the body cavity (FIG. 10). The adapter 65 is also snap fit on the trocar port 94.

Figure 11:
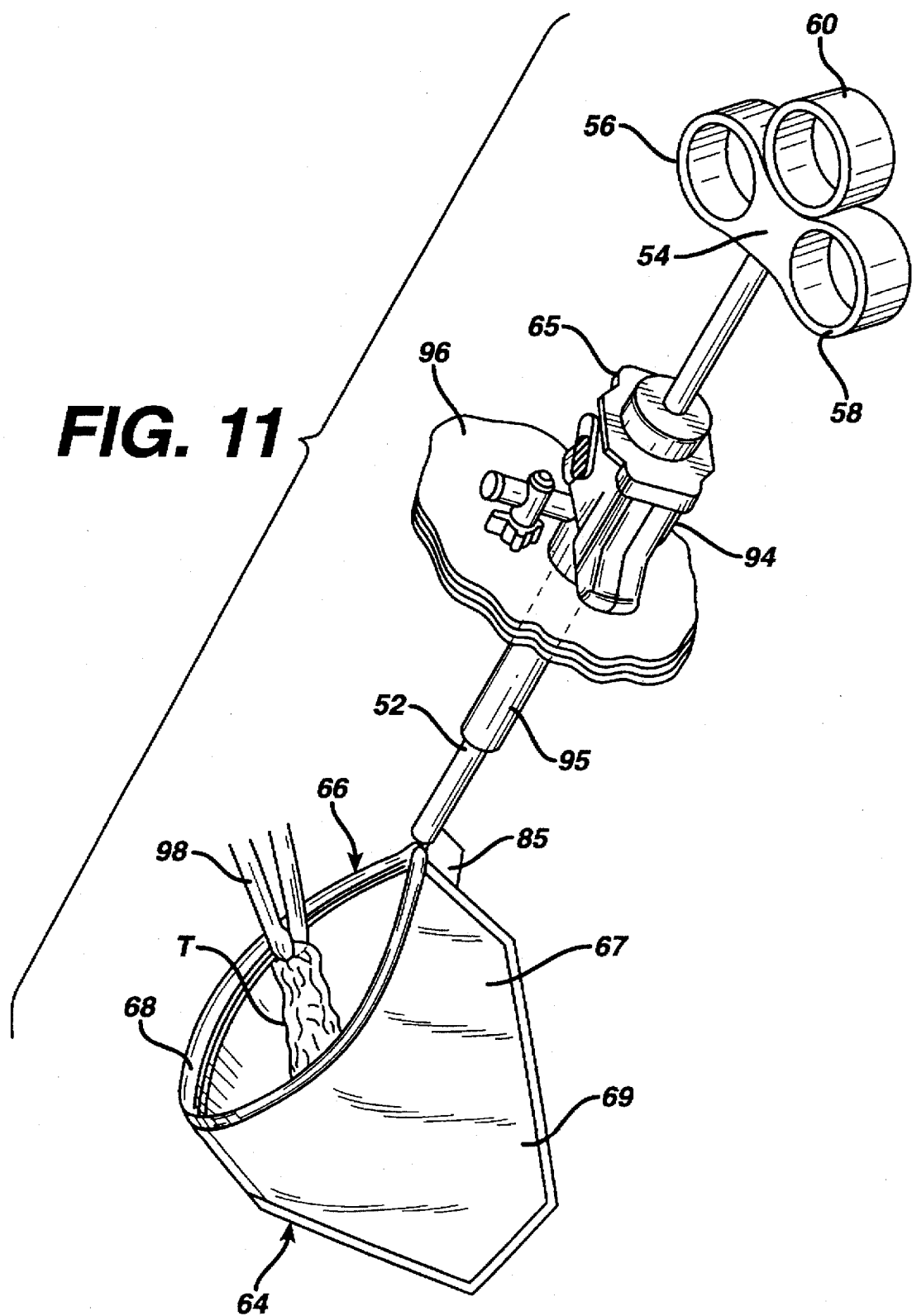

Next, as shown in FIG. 11, the mouth of the pouch 64 is opened by advancing the thumb ring 60 in the distal direction to expand the belt loop 68 from the distal end of the support tube 52. Then, by using a forceps or grasper 98, a tissue specimen T to be retrieved is placed inside the pouch 64. Because the belt loop 68 is substantially rigid, the mouth of the pouch 64 is wide open and the pouch 64 is aligned substantially perpendicular to the loop 68. The pouch 64 can be used as a scoop by manipulation of the support tube 52 to assist in the placement of the tissue T into the pouch 64. Also, by rotating the support tube 52 about its longitudinal axis, the loop 68 at the open mouth of the pouch 64 can be moved into different angular orientations for receiving the tissue T.

Figure 12:
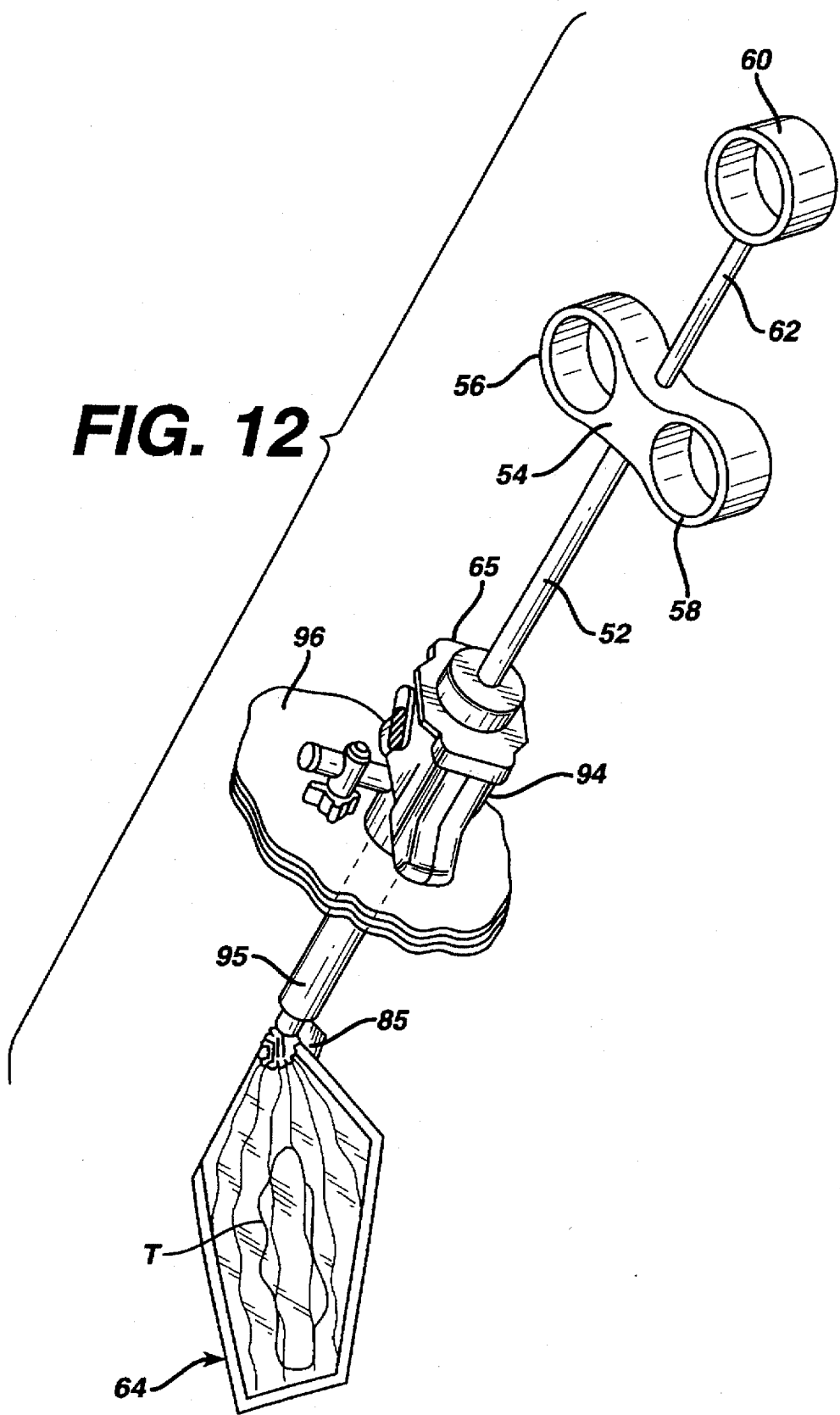
Figure 13:
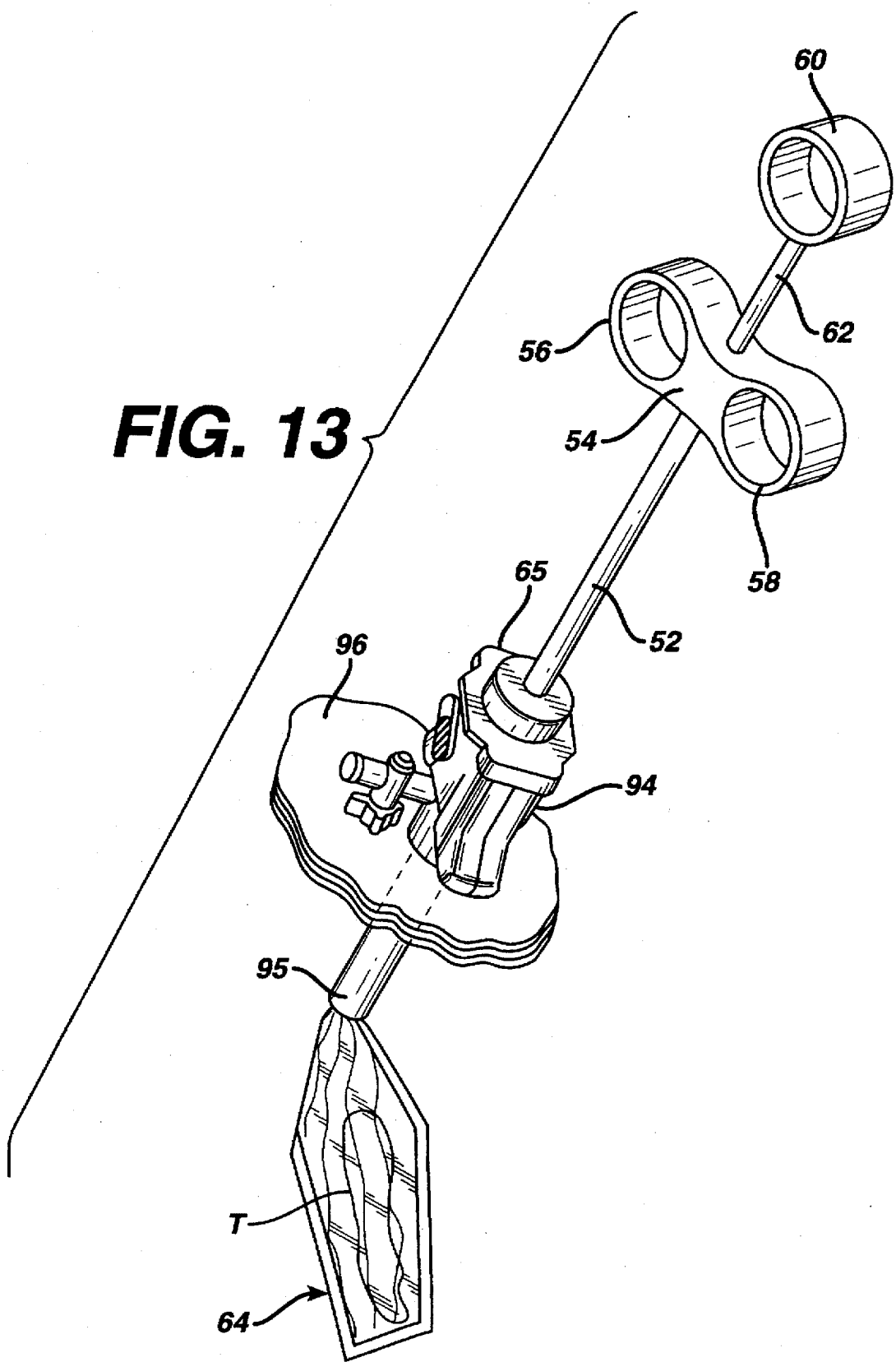
Figure 14:
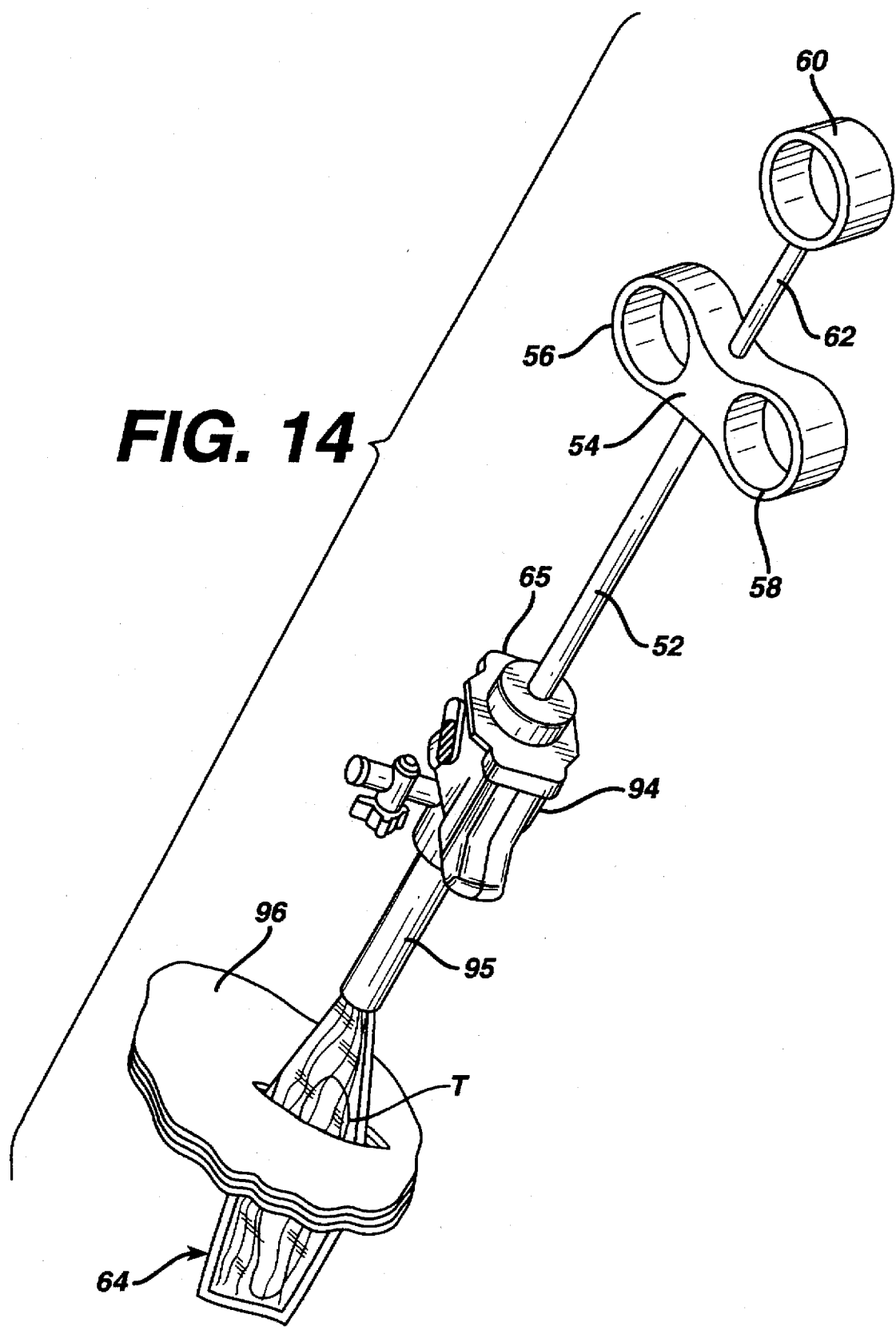

After the tissue T is placed in the pouch 64, the mouth of the pouch 64 is closed by pulling the thumb ring 60 in the proximal direction relative to the finger grip 54 to contract the belt loop 68 into the support tube 52 (FIG. 12). Next, by pulling the thumb ring 60 further in the proximal direction, the top of the pouch 64 is partially drawn into the trocar tube 95 (FIG. 13). Then, by simultaneously pulling the thumb ring 60 and the trocar port 94, the instrument 50 and the trocar tube 95 are withdrawn through the body wall 96 to remove the pouch 64 and the tissue T from the body cavity through the incision at the trocar site (FIG. 14). Preferably, the mouth of the pouch 64 remains inside the trocar tube 95 as the instrument 50 and the trocar port 94 are pulled through the incision in the body wall 96.

Prior to the removal of the instrument 50 from the body cavity, the mouth of the pouch 64 can be reopened, if desired, by advancing the thumb ring 60 in the distal direction to receive another piece of tissue for retrieval from the body cavity. In addition, when the pouch 64 is partially withdrawn from the incision in the body wall 96, the mouth of the pouch 64 can be reopened, if necessary, to allow the tissue specimen to be pulled from the pouch 64 by using the graspers 98.

Figure 2:
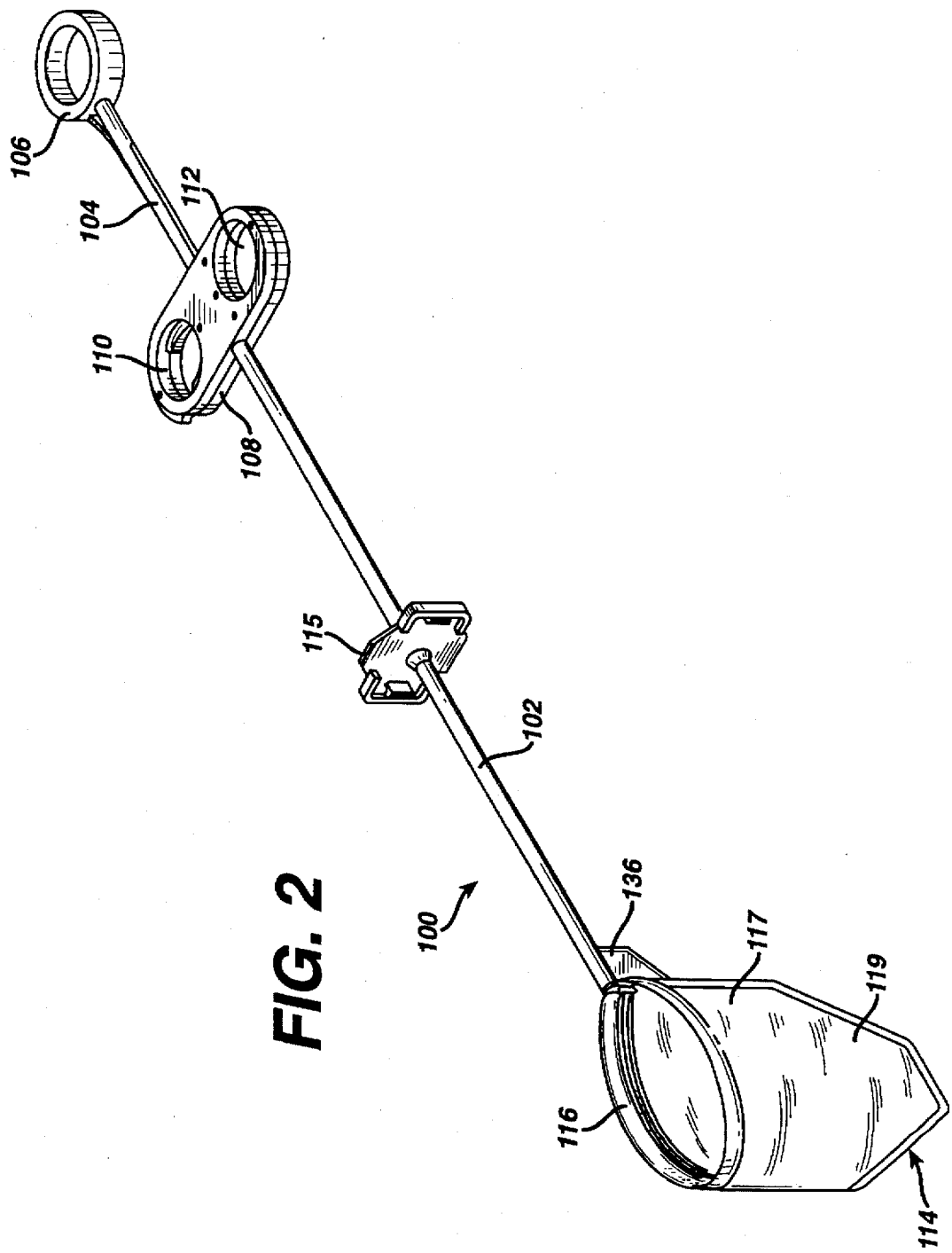
FIG. 2 is a perspective view of a second embodiment of a surgical instrument for retrieving internal body tissue constructed in accordance with this invention.

Referring to FIG. 2, another embodiment of the surgical instrument, generally 100, includes an elongated support tube 102 mounted coaxially on a slide shaft 104 provided with a thumb ring 106 at its distal end. A finger grip 108 including a pair of finger receiving holes 110 and 112 is slidably mounted for axial movement along the slide shaft 104. A collapsible pouch 114 is supported at the distal end of the support tube 102 by a belt 116 which slidably extends through the support tube 102 and is actuated by the slidable finger grip 108.

The pouch 114 has an open top end or mouth for receiving a piece of tissue to be retrieved. The belt 116 is attached abut the open end of the pouch 114 and is slidably extendable through the support tube 102 for expanding the open end of the pouch 114 to receive the tissue and for drawing the open end closed to enclose the tissue in the pouch 114. The distal end of the support tube 102 is sufficiently small in diameter to effectively prevent the pouch material from entering the tube 102 when the mouth of the pouch 114 is cinched by retracting the belt 116 into the tube 102. The support tube 102 is sized for insertion through a trocar or endoscopic tube into a body cavity. An adapter 115 is slidably mounted on the support tube 102. The adapter 115 is arranged to provide a snap fit with the trocar tube and to provide a sliding seal with the support tube 102 to maintain the pressure within the body cavity. With the pouch 114 closed, the surgical instrument 100 is inserted through the trocar or endoscopic tube into the body cavity. After the insertion of the surgical instrument 100 into the body cavity, the pouch 114 is opened and a piece of internal body tissue is placed therein. After the pouch 114 is closed, the surgical instrument 100 is withdrawn from the body cavity with the trocar or endoscopic tube to remove the tissue from the body.

Referring to FIG. 4, the belt 116 is flexed to form a loop 118 extending from the distal end of the support tube 102. The loop 118 is slidably received within a channel 120 which extends along the circumferential length of the open end of the pouch 114. The channel 120 is formed by folding the top portion of the pouch 114 inwardly over itself to provide a circumferential flap 122 which is sealed along its lower edge to the opposed side walls 124 of the pouch 114. The side walls 124 are folded toward each other about a distal edge 126 of the pouch 114. The side walls 124 of the pouch 114 are hermetically sealed together along a proximal edge 128, a bottom edge 130, and a pair of tapered edges 132 and 134. Preferably, the bottom of the pouch 114 is tapered along the edges 132 and 134 to provide a shape which tends to align a piece of tissue placed in the pouch 114 in a convenient orientation for removal through the trocar tube when the pouch 114 is closed and the instrument 100 is withdrawn. The pouch 114 has a proximal flap 136 adjacent to its open top end which is secured to the distal end of the support tube 102, e.g., by glue or other conventional bonding arrangements. Alternatively, the pouch 114 can be secured at its proximal edge by a suture (not shown) which can be threaded through the pouch material and attached at the distal end of the support tube 102.

Preferably, the pouch 114 has a top straight portion 117 with substantially parallel sides and a bottom tapered portion 119 with converging sides. The top straight portion 117 permits the complete expansion of the mouth of the pouch 114 and the belt loop 118. The bottom tapered portion 119 of the pouch 114 forces the tissue specimen to align itself with the length of the pouch 114 and facilitates the removal of the pouch 114 and the tissue specimen from the body cavity through the trocar port site. The tapered shape of the pouch 114 facilitates the removal of the tissue from the body cavity without enlarging the incision at the trocar site. The tapered pouch 114 represents an improvement over a square bottom pouch where the tissue specimen can lay across the width of the pouch and impede removal through the trocar site. The tapered pouch shape also reduces the amount of trapped air, thereby reducing the ballooning effect when the pouch 114 is closed and the stress exerted on the pouch 114 and the abdominal wall tissue at the trocar site.

The belt 116 comprises an elongated flexible member of plastic material which is slidably received in the support tube 102. The belt 116 has an oblong cross section oriented to enhance the stability of the open end of the pouch 114 when the belt 116 is extended. Preferably, the belt 116 is substantially rectangular in cross section with a width larger than its thickness. The larger dimension, i.e., width, of the belt 116 is oriented perpendicular to the plane of the loop 118 and parallel to the side walls 124 of the pouch 114. By movement of the finger grip 108 relative to the slide shaft 104, the belt 116 is extendable from the distal end of the support tube 102 to expand the loop 118 to open the pouch 114 to receive the tissue and is retractable into the support tube 102 to contract the loop 118 to draw the open end of the pouch 114 closed to enclose the tissue therein. Preferably, the pouch 114 and the belt 116 consist of the same polymeric materials mentioned above in connection with the instrument 50.

Figure 15:
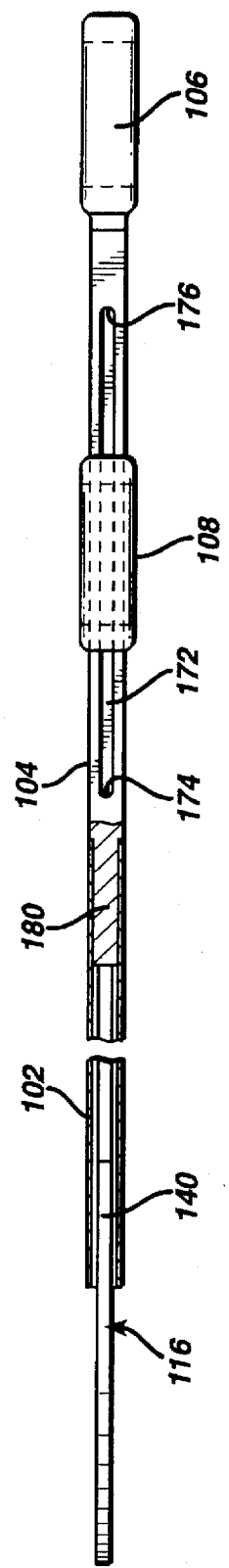
FIG. 15 is a partially cutaway side view of the surgical instrument of FIG. 2.
Figure 16:
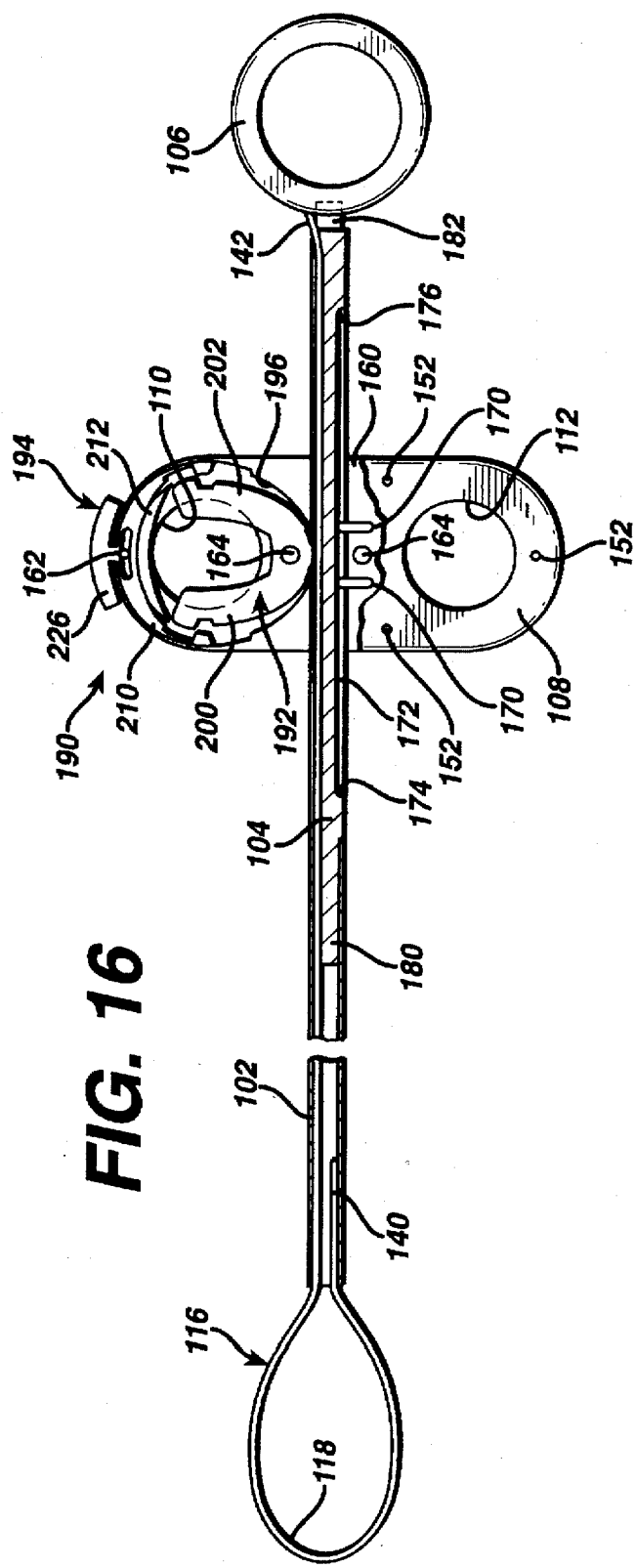
FIG. 16 is a partially cutaway plan view of the surgical instrument of FIG. 2.
Figure 24:
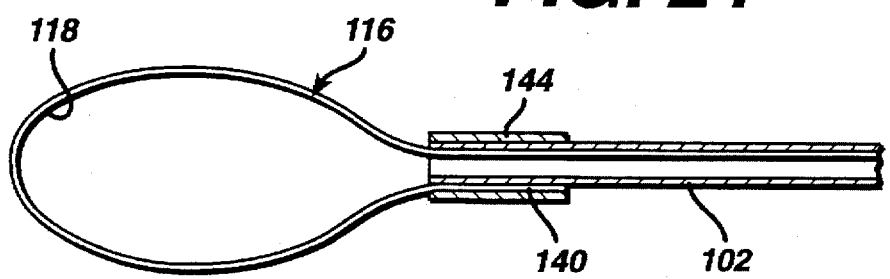
FIG. 24 is a partially cutaway plan view of a modified embodiment of the surgical instrument of this invention.
Figure 25:
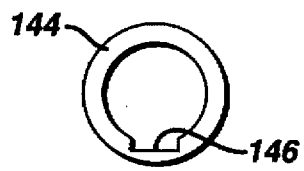
FIG. 25 is a distal end view of a sleeve at the distal end of the instrument of FIG. 24.

In the embodiment of FIGS. 15 and 16, one end 140 of the belt 116 is attached to the support tube 102 adjacent to its distal end. For example, the distal end 140 of the belt 116 can be secured inside the distal end of the support tube 102. The belt 116 is flexed to form the loop 118 and its proximal end 142 extends longitudinally through the support tube 104 and through the slidable finger grip 108. Alternatively, as shown in FIGS. 24 and 25, the distal end 140 of the belt 116 can be attached to the outside of the support tube 102 by a sleeve 144 mounted at the distal end of the support tube 102. The sleeve 144 has an interior longitudinal slot 146 (FIG. 25) in which the distal end 140 of the belt 116 is received and secured to the outside of the support tube 102.

Figure 17:
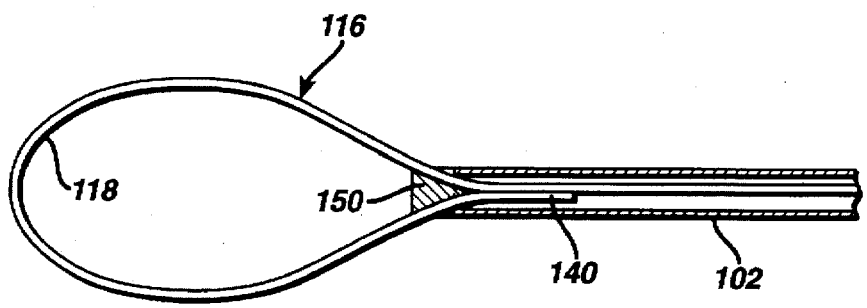
FIG. 17 is a partially cutaway plan view of a modification of the instrument of FIG. 15.
Figure 18:
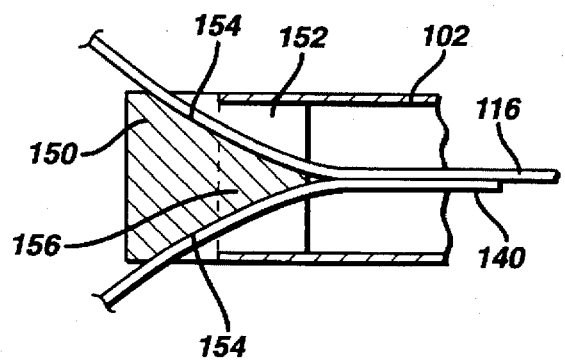
FIG. 18 is an enlarged fragmentary section view of a guide at the distal end of the instrument of FIG. 17.
Figure 19:
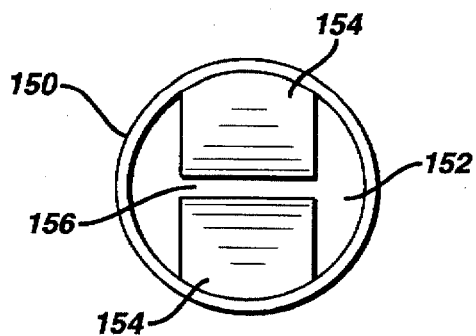
FIG. 19 is a proximal end view of the guide of FIG. 18.

In the modification of FIG. 17, the distal belt end 140 is secured to one side of the belt 116 itself to form the distal belt loop 118. A guide member 150 of generally cylindrical shape has a proximal section 152 of reduced diameter which is secured in the distal end of the support tube 102 (FIG. 18).

The guide member 152 has a pair of ramp-like surfaces 154 formed on its opposite sides which converge in the proximal direction and define a wedge-shaped guide 156 located at the base of the loop 118. The wedge-shaped guide 156 deflects the portions of the belt 116 at the base of the loop 118 outwardly in opposite directions to expand the sides of the loop 118 outward relative to each other. Alternatively, the guide member 150 can be eliminated and a portion of the belt 116 can be preformed into an expanded shape with thermally set curvatures similar to the embodiment shown in FIG. 7 and described above.

Referring to FIG. 2, the slidable finger grip 108 comprises a pair of mating finger grip half-sections 160 which are essentially mirror images of each other. The pair of finger grip half-sections 160 is secured together, e.g., by a plurality of screws 162 and a pair of pins 164 (FIG. 16), with the slide shaft 104 slidably received therebetween. Each of the finger grip half-sections 160 has a central longitudinal channel 166 (FIG. 20) which is semi-circular in cross section. With the finger grip half-sections 160 assembled together (FIG. 21), the channels 166 provide a circular passage extending through the finger grip 108 in which the slide shaft 104 is slidably received.

Figure 20:
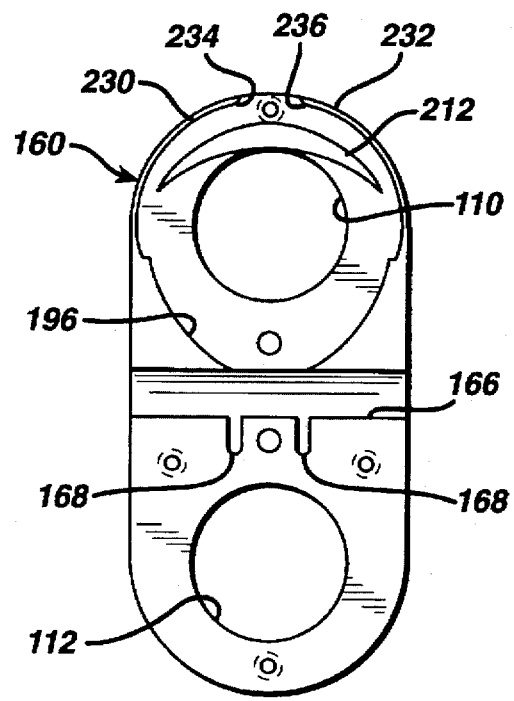
FIG. 20 is a plan view showing the interior of a finger grip of the instrument of FIG. 15.
Figure 21:
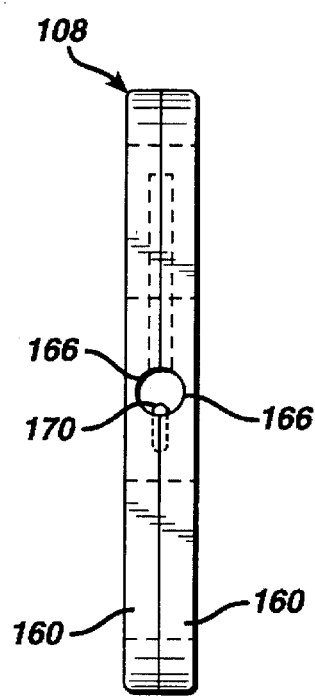
FIG. 21 is a proximal end view showing the sections of the finger grip assembled together.

As shown in FIG. 20, each of the finger grip half-sections 160 includes a pair of longitudinally spaced slots 168 which intersect the channel 166 at right angles. A pair of stop pins 170 (FIG. 16) are inserted in the slots 168 and received in a narrow longitudinal groove 172 formed on one side of the slide shaft 104. The stop pins 170 prevent the finger grip 108 from rotating about the longitudinal axis of the slide shaft 104. Also, the stop pins 170 together with the opposite ends 174 and 176 of the groove 172 provide a stop mechanism to limit the proximal and distal travel of the finger grip 108 along the slide shaft 104.

Figure 22:
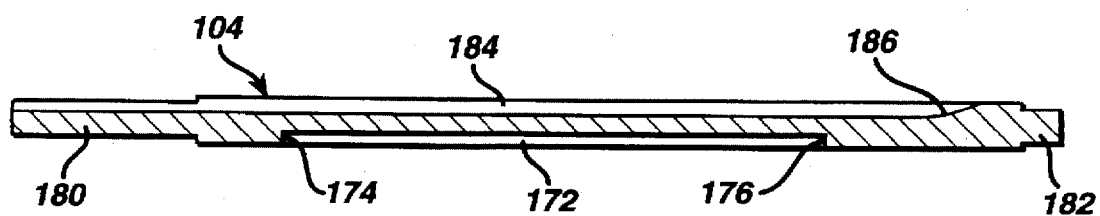
FIG. 22 is a longitudinal section of a slide shaft of the surgical instrument of FIG. 15.
Figure 23:
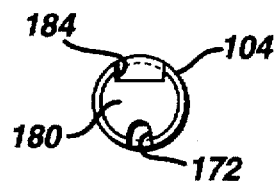
FIG. 23 is an enlarged distal end view of the slide shaft of FIG. 22.

As shown in FIG. 22, the slide shaft 104 has a distal end 180 of reduced diameter which is secured in the proximal end of the support tube 102. Also, the slide shaft 104 has a proximal extension 182 of reduced diameter which is secured to the thumb ring 106. A wide longitudinal channel 184 (FIG. 23) is formed on the opposite side of the slide shaft 104 from the groove 172. The channel 184 extends from the distal end 180 of the slide shaft 104 and terminates at an upwardly sloped ramp 186 adjacent to the proximal end of the slide shaft 104. The belt 116 is slidably received in the channel 184 and its proximal end 144 is directed upwardly by the ramp 186 to allow the belt 116 to slide over the thumb ring 106.

Referring to FIG. 16, a ratchet mechanism, generally 190, including a horseshoe-shaped trigger 192 and an arcuate switch member 194 is mounted on the finger grip 108 for actuating the belt 116. Each finger grip half-section 160 has a generally circular channel 196 for receiving the trigger 192 and switch member 194 of the ratchet mechanism 190. The horseshoe-shaped trigger 192 is pivotally mounted in an inner portion of the circular channel 196 by one of the pins 164 which is received in a pivot hole 198 (FIG. 29) at the vertex of the horseshoe-shaped trigger 192. The trigger 192 has a pair of outwardly diverging arms 200 and 202 which project into the circular opening 110 in the finger grip 108 for actuation by the surgeon.

Figure 30:
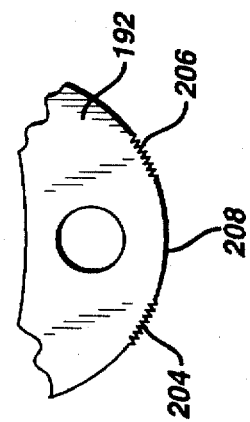
FIG. 30 is an enlarged fragmentary view of the ratchet teeth on the trigger of FIG. 29.

Also, as shown in FIG. 30, the trigger 192 has a first set of ratchet teeth 204 for engaging and driving the belt 116 in the proximal direction and a second set of teeth 206 for engaging and driving the belt 116 in the distal direction. The trigger 192 is normally located in a neutral position (FIG. 27) with both sets of teeth 204 and 206 disengaged from the belt 116. With the trigger 192 in its neutral position, the belt 116 is engaged by a smooth curved surface 208 at the base of the trigger 192 which allows the trigger 192 to slide freely along the belt 116. When the finger grip 108 is reciprocated relative to the slide shaft 104, the trigger 192 is operated in a toggle-like manner under the control of the switch member 194, as described below, to selectively advance or retract the belt 116 relative to the support tube 102.

Figure 27:
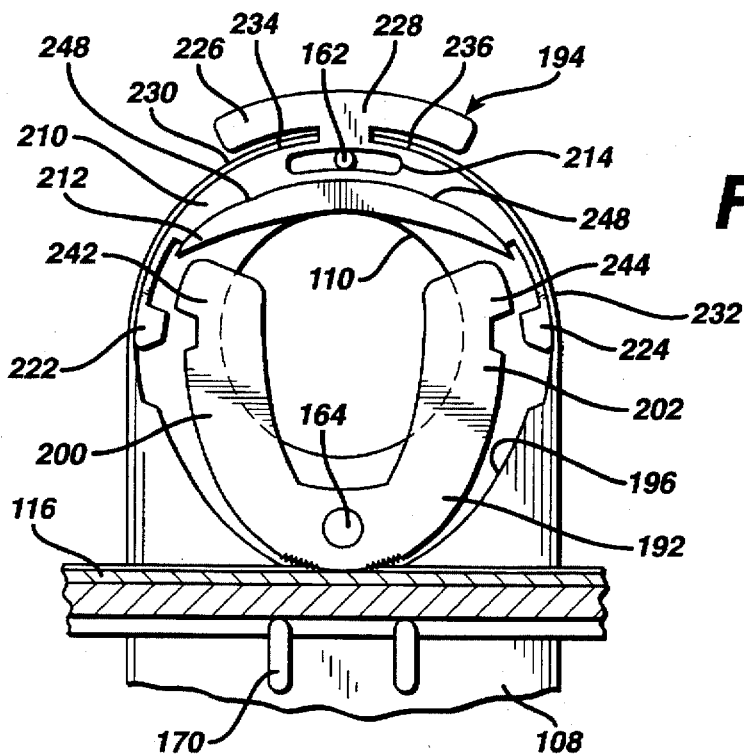
FIG. 27 is an enlarged fragmentary section showing a ratchet mechanism in the finger grip of the surgical instrument of FIG. 15.

As shown in FIG. 27, the switch member 194 has an arcuate switch body 210 which is slidably received in an outer portion of the circular channel 196 adjacent to a crescent-shaped platform 212 formed on each finger grip half-section 160. The arcuate switch body 210 includes an arcuate slot 214 which slidably receives one of the screws 162 connecting the finger grip half-sections 160 together to slidably mount the switch member 194 on the finger grip 108.

Figure 28:
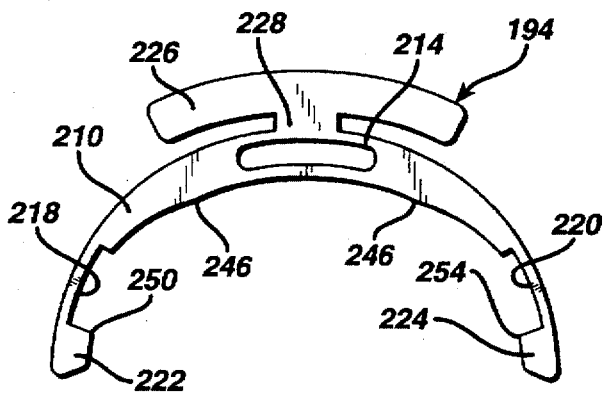
FIG. 28 is an enlarged plan view showing a switch of the ratchet mechanism of FIG. 27.

Referring to FIG. 28, the switch member 194 has a pair of notches 218 and 220 formed adjacent to a pair of control fingers 222 and 224 at the opposite ends of the arcuate switch body 210. The switch member 194 includes an actuator 226 mounted on a stem 228 projecting outwardly from the arcuate switch body 210 and extending between a pair of outer curved walls 230 and 232 (FIG. 27) on each finger grip half-section 160. The outer curved walls 230 and 232 terminate at edges 234 and 236, respectively, which provide forward and reverse stops for engaging the stem 228 to limit the sliding movement of the arcuate switch body 210. Preferably, the outer edge of the actuator 226 has a knurled surface to facilitate actuation by the surgeon.

Figure 29:
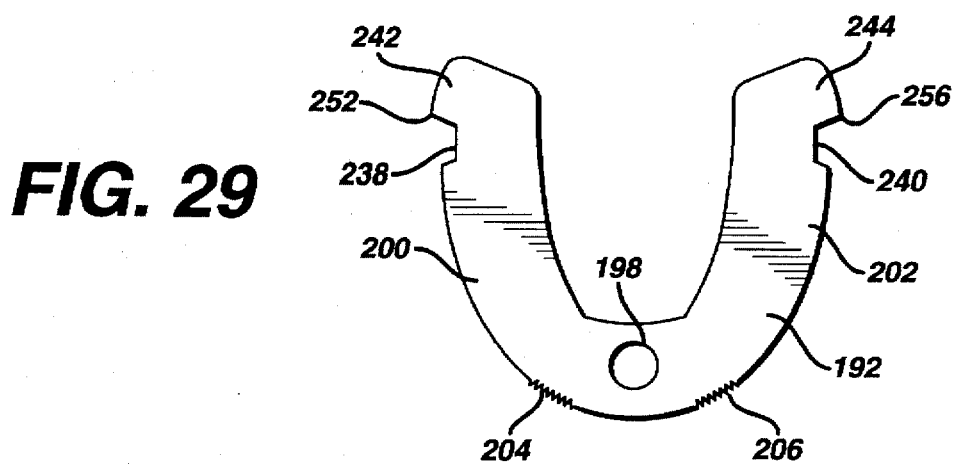
FIG. 29 is an enlarged plan view showing a trigger of the ratchet mechanism of FIG. 27.

Referring to FIG. 29, the trigger 192 has a pair of outwardly facing notches 238 and 240 which define a pair of outwardly projecting tabs 242 and 244, respectively, on the trigger arms 200 and 202. The tabs 242 and 244 of the trigger 192 cooperate with the control fingers 222 and 224 (FIG. 28) on the switch member 194, in the manner described below, to control the direction of movement of the belt 116 in response to the reciprocation of the finger grip 108 relative to the slide shaft 104.

The switch member 194 controls the pivoting of the trigger 192 to determine which set of teeth 204 or 206 engage the belt 116 when the finger grip 108 is reciprocated along the slide shaft 104. The switch member 194 has a neutral position (FIG. 27) in which the trigger 192 is maintained in its neutral position with both sets of teeth 204 and 206 disengaged from the belt 116. The control fingers 222 and 224 of the switch member 194 are aligned with the tabs 242 and 244 of the trigger 22 to restrict the pivoting of the trigger 192, either clockwise or counterclockwise, to prevent the engagement of the teeth 204 and 206 with the belt 116. The counterclockwise pivoting of the trigger 192 is limited by engagement of an upper edge 250 (FIG. 28) of the control finger 222 with a lower edge 252 (FIG. 29) of the tab 242. Similarly, the clockwise pivoting of the trigger 192 is limited by the engagement of an upper edge 254 of the control finger 224 with a lower edge 256 of the tab 244. When the finger grip 108 is reciprocated relative to the slide shaft 104 with the switch member 194 in the neutral position, the trigger 192 merely slides along the belt 116 without advancing or retracting the belt 116 relative to the support tube 102.

The switch member 194 includes a pair of bumps 246 (FIG. 28) formed on the inner concave edge of the arcuate switch body 210. The bumps 246 engage a corresponding set of depressions 248 formed in the outer convex edge of the arcuate platform 212 when the switch member 194 is set to its neutral position. The bumps 246 and depressions 248 provide an alignment mechanism which allows the switch member 194 to be accurately located in its neutral position.

Figure 32:
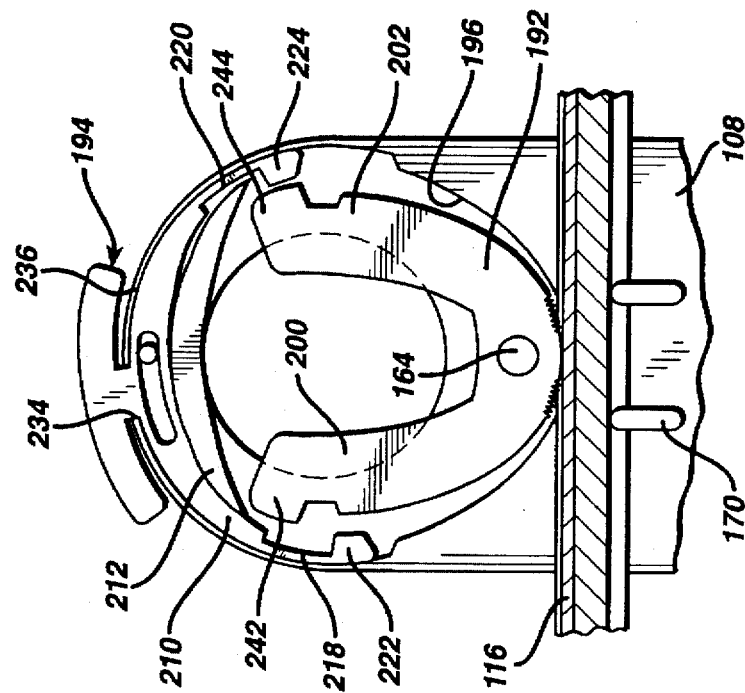
FIGS. 31 and 32 illustrate the operation of the ratchet mechanism of FIG. 27.
Figure 31:
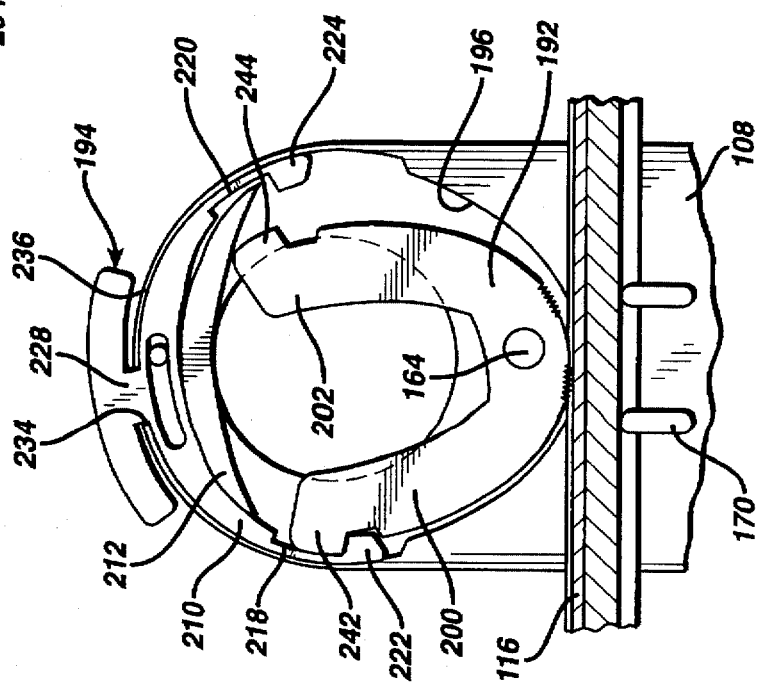

When it is desired to advance the belt 116 to open the pouch 114, the switch member 194 is set to its advance position (FIG. 31) with the switch stem 228 engaged with the forward stop 234 on the finger grip 108. With the switch member 194 in its advance position, the notch 218 and the control finger 222 are positioned to allow full pivoting of the trigger 192 in the counterclockwise direction during the forward stroke of the finger grip 108. Also, the control finger 224 is positioned to engage the tab 244 to maintain the trigger 192 in its neutral position during the proximal stroke of the finger grip 108. Thus, when the finger grip 108 is reciprocated relative to the slide shaft 104, the trigger 192 is actuated in a toggle-like manner, shown in FIGS. 31 and 32, in which the trigger 192 pivots alternately between its advance position with the teeth 204 engaged with the belt 116 and its neutral position with the teeth 204 disengaged from the belt 116. As a result, each time the finger grip 108 is reciprocated, the belt 116 is engaged and advanced by the teeth 204 during the distal stroke, and the teeth 204 are disengaged from the belt 116 during the proximal stroke to allow the trigger 192 to slide proximally over the belt 116 which remains in its advanced position.

When it is desired to retract the belt 116 into the support tube 102 to close the pouch 114, the switch member 194 is set to its retract position with the switch stem 228 engaged with the reverse stop 236. When the finger grip 108 is reciprocated relative to the slide shaft 104, the trigger 192 is operated in a toggle-like manner in which the trigger member 192 is alternately pivoted between its reverse position with the teeth 206 engaged with the belt 116 and its neutral position with the teeth 206 disengaged from the belt 116. As a result, each time the finger grip 108 is reciprocated, the belt 116 is engaged and retracted by the teeth 206 during the proximal stroke, and the teeth 206 are disengaged from the belt 116 in the distal stroke to allow the trigger 192 to slide distally over the belt 116 which remains in its retracted position.

The operation of the instrument 116 to retrieve a piece of internal body tissue through a trocar port is substantially the same as the operation of the instrument 50 (FIGS. 9–14) described above. Prior to the insertion of the instrument 100 into the trocar tube, the open end of the pouch 114 is closed by reciprocating the finger grip 108 along the slide shaft 104 with the switch member 194 set to its retract position to contract the belt loop 118 into the support tube 102. Then, with the pouch 114 aligned with the longitudinal axis of the support tube 102, the distal end of the support tube 102 is inserted into the trocar tube and advanced until the pouch 114 exits from the trocar tube into the body cavity. The adapter 115 is snap fit on the trocar port.

Next, the mouth of the pouch 114 is opened by reciprocating the finger grip 108 along the slide shaft 104 with the switch member 194 set to its advance position to expand the belt loop 118 from the distal end of the support tube 102. Then, by using a forceps or grasper, the tissue to be retrieved is placed inside the pouch 114. After the tissue is placed in the pouch 114, the pouch 114 is closed by reciprocating the finger grip 108 relative to the slide shaft 104 with the switch member 194 set to the retract position to contract the belt loop 118 into the support tube 102. Next, by pulling the thumb ring 106 in the proximal direction, the top of the pouch 114 is partially drawn into the trocar tube. Then, by pulling the thumb ring 106 and the trocar port in the proximal direction, the instrument 100 and the trocar port are withdrawn through the body wall to remove the pouch 114 and the tissue from the body cavity through the incision at the trocar site.

Figure 26:
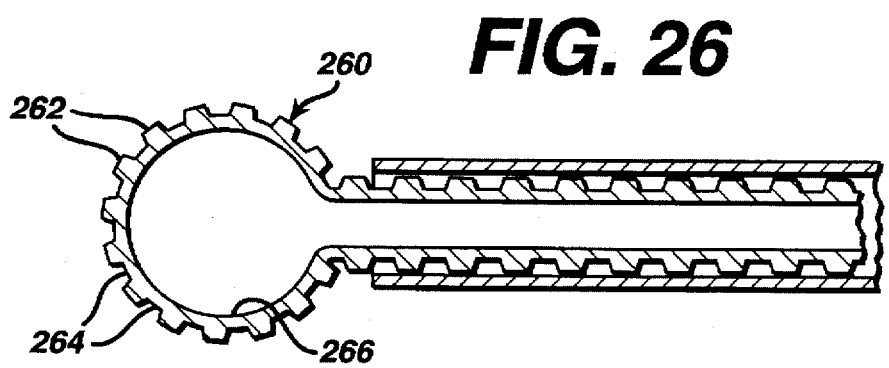
FIG. 26 is a partially cutaway plan view of a further embodiment of the surgical instrument of this invention.

In the modification of FIG. 26, a flexible belt 260 is formed with alternating thick and thin regions 262 and 264, respectively, similar to a timing belt with teeth. Each of the thick regions 262 and the thin regions 264 extends transversely across the width of the belt 260 and is oriented perpendicular to the plane of the belt loop 266. The thick regions 262 enhance the stiffness of the belt 260 across its width to prevent the loop 266 from bending when it is used to scoop in a piece of tissue. The thin regions 264 allow the loop 266 to bend into a smaller diameter without deformation of the belt material. With the ribbed configuration of belt 260, it has been found that when the thick regions 262 are longer than the thin regions 264, the belt 260 recovers more completely after bending of the belt 260. It is contemplated that the ribbed belt 260 can be used in place of the belts 66 and 116 described in the above embodiments. An example of a ribbed belt 260 which can be used in the surgical instruments of the present invention is made by Brecoflex Corp. of Eatontown, N.J., #3 mm MXL.

FIGS. 33–36 show examples of the elongated tapered pouch configurations which can be employed in the surgical tissue retrieval instruments 50 and 100 described above. Generally, it has been found desirable to construct the pouch with an elongated configuration such that the length or depth of the pouch is substantially greater than the width of the pouch at its mouth. Preferably, the ratio of the length or depth of the pouch to the width of the pouch at its mouth is 1½ to 1 or more. The advantage of using an elongated pouch is that the tissue placed in the pouch tends to become aligned with the larger dimension (length or depth) of the pouch. When the pouch is closed and withdrawn from the body cavity with the trocar tube, the elongated pouch is aligned longitudinally along the axis of the trocar tube to facilitate the passage of the pouch and the tissue through the incision in the body wall at the trocar port site. The use of an elongated pouch minimizes the possibility of the tissue being oriented transversely, i.e., across the width of the pouch, rather than being aligned longitudinally along its length or depth. Thus, the elongated pouch avoids the problem of the tissue assuming a crosswise orientation in the pouch and interfering with the withdrawal of the closed pouch and tissue through the incision at the trocar port site.

Figure 33:
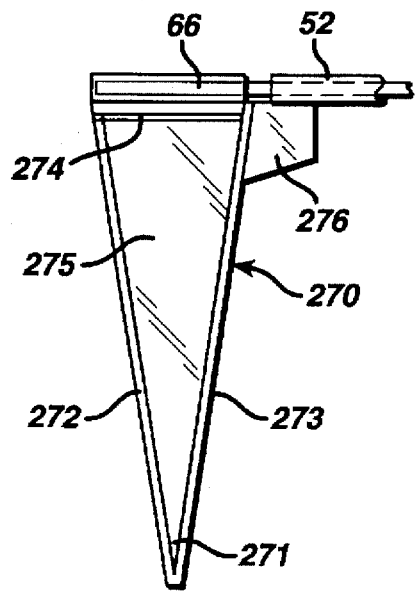
FIGS. 33–36 show various configurations of the pouch employed in the surgical tissue retrieval instruments of the present invention.

Referring to FIG. 33, one example of an elongated pouch 270 has an elongated V-shaped configuration which tapers to a point 271 at the bottom. The pouch 270 consists of a pair of triangular pieces of polymeric material which are thermally bonded together along its tapered edges 272 and 273. On the front and back of the pouch 270, the top of the pouch material is folded inwardly over itself to provide a top flap 274 which is sealed along its lower edge to a side wall 275 of the pouch 270. Each of the flaps 274 defines a channel in which the belt 66 is slidably received. The pouch 270 has a proximal flap 276 adjacent to its open top end which is secured to the distal end of the support tube 52. By way of example, a first embodiment of the pouch 270 is six inches high and two inches wide at its mouth. A second embodiment of the pouch 270 is eight inches high and one and one-half inches wide at its mouth.

Figure 34:
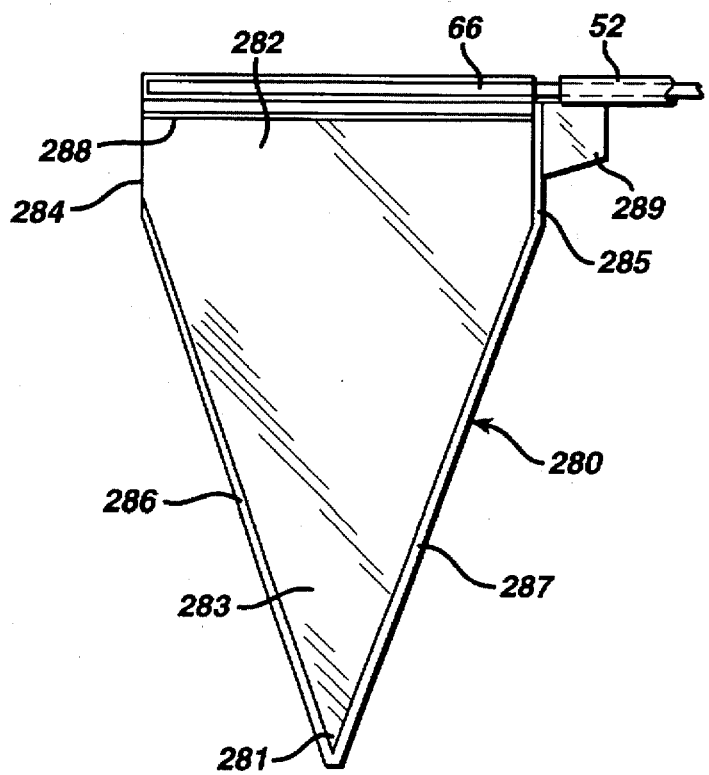
Figure 35:
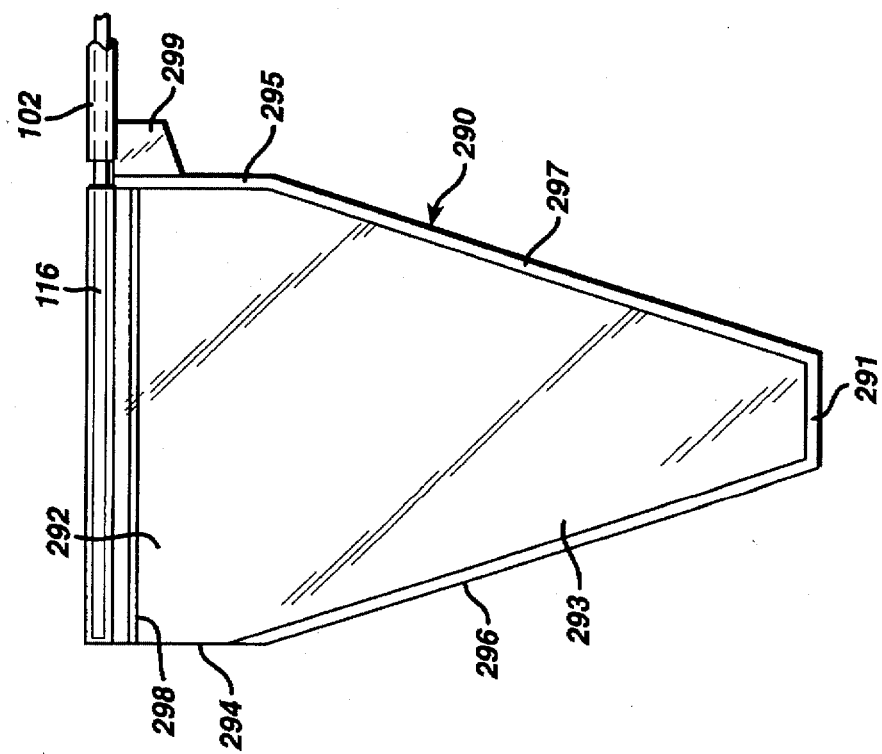
Figure 36:
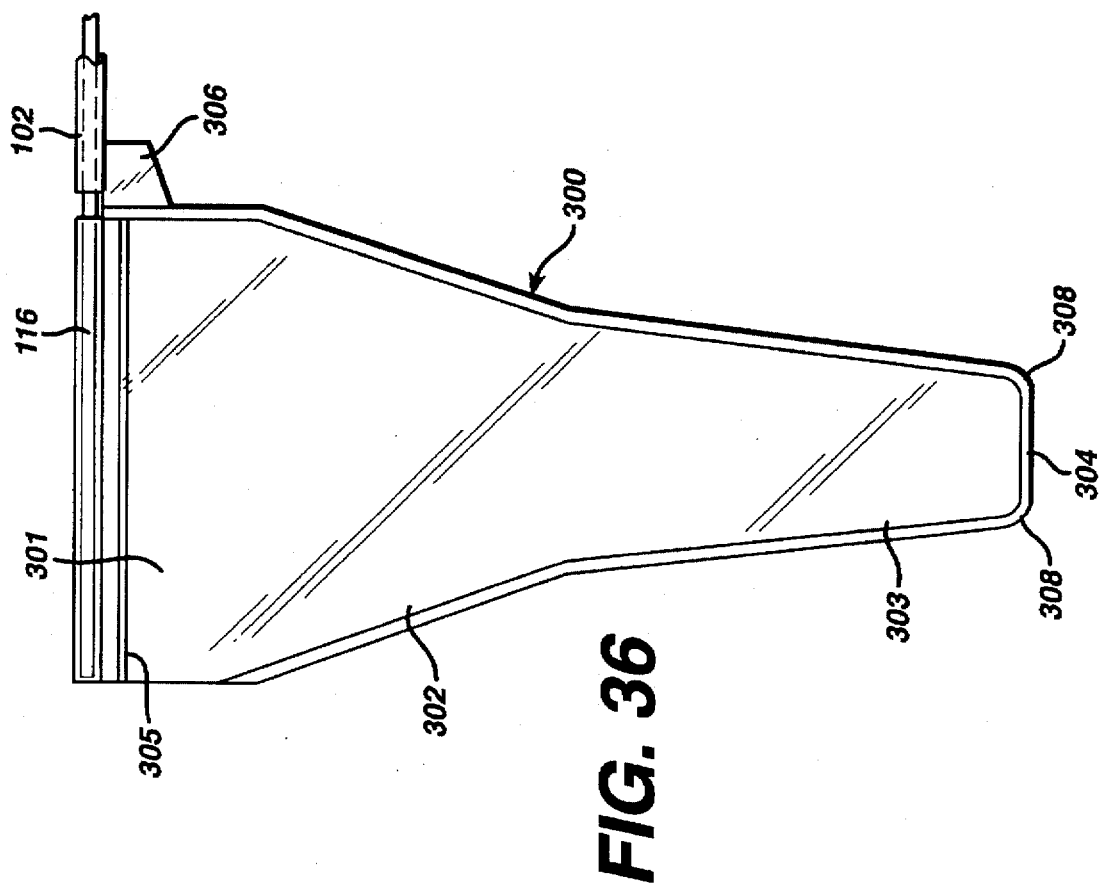

To permit the complete expansion of the mouth of the pouch and the belt, it is advantageous to construct the pouch with straight sides which are parallel to each other adjacent to the mouth to avoid restriction on the opening of the pouch when the belt loop is expanded. This construction is particularly desirable for larger pouches having widths of four inches or more and lengths of four to eight inches or more. The pouches of FIGS. 34–36 are examples of larger pouches each having a straight portion with parallel sides near the mouth of each pouch. On smaller pouches, e.g., widths of two inches or less and lengths of six to eight inches or more, it has been found that the straight or parallel portion can be omitted. The pouch 270 of FIG. 33 is an example of a smaller pouch without a straight or parallel portion at the mouth of the pouch.

As shown in FIG. 34, another example of an elongated pouch 280 has an elongated V-shaped configuration which tapers to a point 281 at the bottom of the pouch 280. The pouch 280 has an upper straight portion 282 with parallel sides adjacent to its mouth and a lower tapered portion 283 with converging sides. The pouch 280 consists of a single piece of polymeric material which is folded along a distal edge 284 and hermetically sealed along a proximal edge 285 and a pair of tapered edges 286 and 287. The distal edge 284 of the pouch 280 is parallel to its proximal edge 285. At the top of the pouch 280, the pouch material is folded inwardly over itself to provide a top flap 288 which is sealed along its lower edge to the upper portion 282 of the pouch 280. The top flap 288 defines a circumferential channel in which the belt 66 is slidably received. The pouch 280 has a proximal flap 289 adjacent to its open top end which is secured to the distal end of the support tube 52. By way of example, the pouch 280 is four inches wide at its mouth while the upper straight portion 282 is one and one-half inches high and the lower tapered portion 283 is six inches high.

Referring to FIG. 35, another example of an elongated tapered pouch 290 is truncated in shape and terminates at a narrow bottom edge 291 which is parallel to the mouth of the pouch 290. The pouch 280 has an upper straight portion 292 with parallel sides adjacent to its mouth and a lower tapered portion 293 with converging sides. The pouch 290 consists of a single piece of polymeric material which is folded along a distal edge 294 and hermetically sealed along a proximal edge 295 and a pair of tapered edges 296 and 297. The distal edge 294 of the pouch 290 is parallel to its proximal edge 295. At the top of the pouch 290, the pouch material is folded inwardly over itself to provide a top flap 298 which is sealed along its lower edge to the upper portion 292 of the pouch 290. The top flap 298 defines a circumferential channel in which the belt 116 is slidably received. The pouch 280 has a proximal flap 299 adjacent to its open top end which is secured to the distal end of the support tube 102. Preferably, the width of the pouch 290 at its bottom edge 291 is one-third or less than the width of the pouch 290 at its mouth. By way of example, the pouch 290 is six inches wide at its mouth and one and one-half inches wide at its bottom edge 291, while its upper straight portion 292 is two inches high and its lower tapered portion 293 is seven inches high.

As shown in FIG. 36, another example of an elongated pouch 300 is tapered at multiple angles to allow the tissue to be placed further down in the pouch 300. The pouch 300 has an upper straight portion 301, an intermediate tapered portion 302 and a lower tapered portion 303 which terminates at a bottom edge 304 parallel to the mouth of the pouch 300. The intermediate portion 302 is tapered more sharply than the lower portion 303. At the top of the pouch 300, the pouch material is folded inwardly over itself to provide a top flap 305 which is sealed along its lower edge to the upper portion 301 of the pouch 300. The top flap 305 defines a circumferential channel in which the belt 116 is slidably received. The pouch 300 has a proximal flap 306 adjacent to its open top end which is secured to the distal end of the support tube 102. Preferably, the width of the pouch 300 at its bottom edge 304 is one-third or less than the width of the pouch 300 at its mouth. The bottom edge 304 of the pouch 300 has rounded corners 308. By way of example, the pouch 300 is six inches wide at its mouth and two inches wide at its bottom edge 304. The upper straight portion 301 is two inches high, the intermediate tapered portion 302 is four inches high, and the lower tapered portion 303 is six inches high.

The invention in its broader aspects is not limited to the specific details of the preferred embodiments shown and described, and those skilled in the art will recognize that the invention can be practiced with modification within the spirit and scope of the appended claims.

We claim:

1. A surgical instrument for retrieving tissue, comprising:
   an elongated support shaft;
   a collapsible pouch supported at the distal end of said support shaft and having an open end for receiving the tissue to be retrieved; and
   a belt attached about said open end of said pouch and slidable longitudinally relative to said support shaft for expanding said open end of said pouch to receive the tissue and for drawing said open end closed to enclose the tissue in said pouch, wherein said belt has a ribbed configuration with alternating thick and thin regions extending transversely across the width of said belt.

2. The surgical instrument of claim 1, which includes actuator means for moving said belt relative to said shaft to open and close said pouch, and wherein said actuator means includes:
   a reciprocating finger grip slidably mounted for longitudinal movement relative to said support shaft; and
   a ratchet mechanism on said finger grip for selectively advancing and retracting said belt to expand and contract said loop.

3. A surgical instrument for retrieving internal body tissue, comprising:
   an elongated support tube;
   a collapsible pouch supported at the distal end of said support tube and having an open end for receiving the tissue to be retrieved;
   a belt formed into a loop slidably attached about said open end of said pouch, said belt being slidably extendable through said support tube for expanding said open end of said pouch to receive the tissue and retractable into said support tube for drawing said open end closed to enclose the tissue in said pouch, wherein said belt has a ribbed configuration with alternating thick and thin regions extending transversely across the width of said belt; and
   actuator means for moving said belt relative to said support tube to open and close said pouch, wherein said actual means includes:
   a reciprocating finger grip slidably mounted for longitudinal movement relative to said support tube; and,
   a ratchet mechanism on said finger grip for selectively advancing and retracting said belt to expand and contract said loop, wherein said ratchet mechanism includes:
   a trigger pivotally mounted on said finger grip and including first teeth for engaging and advancing said belt and second teeth for engaging and retracting said belt relative to said support tube; and
   a switch for controlling the pivoting of said trigger to determine which teeth engage said belt when said finger grip is reciprocated.

4. A surgical instrument for retrieving tissue, comprising:

an elongated support shaft;

a collapsible pouch supported at the distal end of said support shaft and having an open end for receiving the tissue to be retrieved;

a belt formed into a loop slidably attached about said open end of said pouch, said belt being slidably longitudinally relative to said support shaft for expanding said open end of said pouch to receive the tissue and for drawing said open end closed to enclose the tissue in said pouch; and ratchet means on said shaft for moving said belt relative to said shaft to open and close said pouch, wherein said ratchet means comprises:

a reciprocating finger grip slidably mounted for longitudinal movement relative to said shaft; and a ratchet mechanism on said finger grip for selectively advancing and retracting said belt to expand and contract said open end of said pouch, wherein said ratchet mechanism includes:

a trigger pivotally mounted on said finger grip and including first teeth for engaging and advancing said belt and second teeth for engaging and retracting said belt relative to said support shaft; and a switch for controlling the pivoting of said trigger to determine which teeth engage said belt when said finger grip is reciprocated; and, wherein said ratchet mechanism includes:

a finger actuated trigger pivotally mounted on said finger grip and including first teeth for engaging and advancing said belt when said trigger is pivoted to a first position and second teeth for engaging and retracting said belt when said trigger is pivoted to a second position, said trigger being normally located in a neutral position with both of said teeth disengaged from said belt; and a switch mounted on said finger grip for controlling the pivoting of said trigger to control which teeth engage said belt when said finger grip is reciprocated, said switch having a neutral position in which said trigger is maintained in its neutral position, a first operative position in which said trigger is pivotable in a toggle-like manner between its neutral position and its first position when said finger grip is reciprocated to advance said belt and expand said loop, and a second operative position in which said trigger is pivotable in a toggle-like manner between its neutral position and its second position when said finger grip is reciprocated to retract said belt and contract said loop.

5. The surgical instrument of claim 4, wherein said ratchet means comprises:

a reciprocating finger grip slidably mounted for longitudinal movement relative to said shaft; and a ratchet mechanism on said finger grip for selectively advancing and retracting said belt to expand and contract said open end of said pouch.

6. A surgical instrument for retrieving internal body tissue, comprising:

an elongated support tube;

a collapsible pouch supported at the distal end of said support tube and having an open end for receiving the tissue to be retrieved;

a belt formed into a loop slidably attached about said open end of said pouch, said belt being slidably extendable through said support tube for expanding said open end of said pouch to receive the tissue and retractable into said support tube for contracting said open end to enclose the tissue in said pouch; and ratchet means on said support tube for moving said belt relative to said tube to open and close said pouch wherein said ratchet means comprises:

a reciprocating finger grip slidably mounted for longitudinal movement relative to said support tube; and a ratchet mechanism on said finger grip for selectively advancing and retracting said belt to expand and contract said loop wherein said ratchet mechanism includes:

a trigger pivotally mounted on said finger grip and including first teeth for engaging and advancing said belt and second teeth for engaging and retracting said belt relative to said support tube; and a switch for controlling and pivoting of said trigger to determine which teeth engage said belt when said finger grip is reciprocated; and, wherein said ratchet mechanism includes:

a finger actuated trigger pivotally mounted on said finger grip and including first teeth for engaging and advancing said belt when said trigger is pivoted to a first position and second teeth for engaging and retracting said belt when said trigger is pivoted to a second position, said trigger being normally located in a neutral position with both of said teeth disengaged from said belt; and a switch mounted on said finger grip for controlling the pivoting of said trigger to control which teeth engage said belt when said finger grip is reciprocated, said switch having a neutral position in which said trigger is maintained in its neutral position, a first operative position in which said trigger is pivotable in a toggle-like manner between its neutral position and its first position when said finger grip is reciprocated to advance said belt and expand said loop, and a second operative position in which said trigger is pivotable in a toggle-like manner between its neutral position and its second position when said finger grip is reciprocated to retract said belt and contract said loop.

* * * * *